(12) United States Patent
Collette

(10) Patent No.: US 7,805,852 B2
(45) Date of Patent: Oct. 5, 2010

(54) SIGHTING INSTRUMENT FOR DETERMINING THE MECHANICAL AXIS OF THE FEMUR

(76) Inventor: Michel Collette, 11 avenue du Marechal, Brussels (BE) B-1180

( * ) Notice: Subject to any disclaimer, the term of this patent is extended or adjusted under 35 U.S.C. 154(b) by 291 days.

(21) Appl. No.: 11/913,718

(22) PCT Filed: May 8, 2006

(86) PCT No.: PCT/BE2006/000049

§ 371 (c)(1),
(2), (4) Date: Jun. 20, 2008

(87) PCT Pub. No.: WO2006/119591

PCT Pub. Date: Nov. 16, 2006

(65) Prior Publication Data

US 2009/0216247 A1    Aug. 27, 2009

(30) Foreign Application Priority Data

May 6, 2005    (FR)    ................................. 05 04607

(51) Int. Cl.
A61B 1/00    (2006.01)
A61B 17/58    (2006.01)
(52) U.S. Cl. .......................................... 33/511; 33/512
(58) Field of Classification Search ............. 33/511, 33/512; 600/414, 587; 606/88, 89, 102
See application file for complete search history.

(56) References Cited

U.S. PATENT DOCUMENTS

| 762,146 | A | * | 6/1904 | Cosbie | 33/511 |
|---|---|---|---|---|---|
| 4,349,018 | A | * | 9/1982 | Chambers | 606/88 |
| 4,457,307 | A | * | 7/1984 | Stillwell | 606/88 |
| 4,989,337 | A | * | 2/1991 | Mason et al. | 33/512 |
| 5,007,912 | A | | 4/1991 | Albrektsson et al. | |
| 5,148,606 | A | * | 9/1992 | Mason et al. | 33/512 |
| 5,314,429 | A | * | 5/1994 | Goble | 606/96 |
| 5,376,093 | A | * | 12/1994 | Newman | 606/88 |
| 5,520,694 | A | | 5/1996 | Dance et al. | |

(Continued)

FOREIGN PATENT DOCUMENTS

FR    2 829 376 A1    3/2003

OTHER PUBLICATIONS

International Search Report of PCT/BE2006/000049 filed May 8, 2006, date of mailing Aug. 24, 2006.

*Primary Examiner*—Yaritza Guadalupe-McCall
(74) *Attorney, Agent, or Firm*—Young & Thompson

(57) ABSTRACT

A device for the determination of a plane containing the mechanical axis of the femur includes a mechanical member of articulated and or/sliding elements for the determination and memorization of two positions in space (F1 and F2) of the same point (F) of the knee, freely selected, when the knee is in position P1 and P2, relative to a referential system. These positions are obtained by rotation of the inferior limb from position P1 to position P2, about the centre of the femoral head. The orientation of an omega plan perpendicular to the frontal or sagittal plane containing the centre of the femoral head and the centre of the knee can be materialized by a rod contained in this plane, which rod is fixed perpendicularly and in the middle of the arm having at the ends two localization elements for points F1 and F2.

23 Claims, 27 Drawing Sheets

U.S. PATENT DOCUMENTS

| | | | |
|---|---|---|---|
| 5,540,696 A * | 7/1996 | Booth et al. | 606/88 |
| 5,611,353 A | 3/1997 | Dance et al. | |
| 5,643,272 A * | 7/1997 | Haines et al. | 606/80 |
| 5,776,137 A * | 7/1998 | Katz | 606/88 |
| 5,810,831 A * | 9/1998 | D'Antonio | 606/88 |
| 6,013,081 A * | 1/2000 | Burkinshaw et al. | 606/88 |
| 6,024,746 A * | 2/2000 | Katz | 606/88 |
| 6,077,270 A * | 6/2000 | Katz | 606/88 |
| 6,193,724 B1 * | 2/2001 | Chan | 606/102 |
| 6,554,837 B1 | 4/2003 | Hauri et al. | |
| 6,595,997 B2 * | 7/2003 | Axelson et al. | 606/88 |
| 6,979,299 B2 * | 12/2005 | Peabody et al. | 600/587 |
| 7,241,298 B2 * | 7/2007 | Nemec et al. | 606/86 R |
| 7,335,167 B1 * | 2/2008 | Mummy | 600/587 |
| 7,455,647 B2 * | 11/2008 | Tarabichi | 600/587 |
| 7,488,324 B1 * | 2/2009 | Metzger et al. | 606/89 |
| 7,695,479 B1 * | 4/2010 | Metzger | 606/102 |
| 2003/0149378 A1 * | 8/2003 | Peabody et al. | 600/587 |
| 2005/0020941 A1 * | 1/2005 | Tarabichi | 600/587 |
| 2005/0059980 A1 * | 3/2005 | Overes | 606/102 |
| 2007/0185498 A2 * | 8/2007 | Lavallee | 606/102 |
| 2008/0139965 A1 * | 6/2008 | Meneghini et al. | 600/587 |
| 2008/0306484 A1 * | 12/2008 | Coon et al. | 606/88 |
| 2009/0216247 A1 * | 8/2009 | Collette | 606/130 |
| 2009/0299376 A1 * | 12/2009 | Martinez et al. | 606/102 |
| 2010/0099977 A1 * | 4/2010 | Hershberger | 600/414 |
| 2010/0100011 A1 * | 4/2010 | Roche | 600/587 |

* cited by examiner

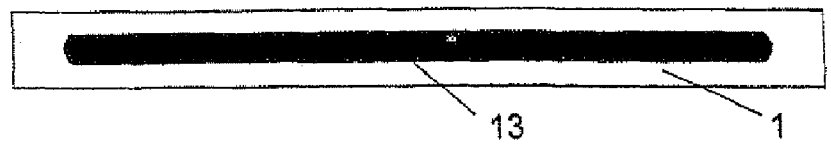
FIG. 7a
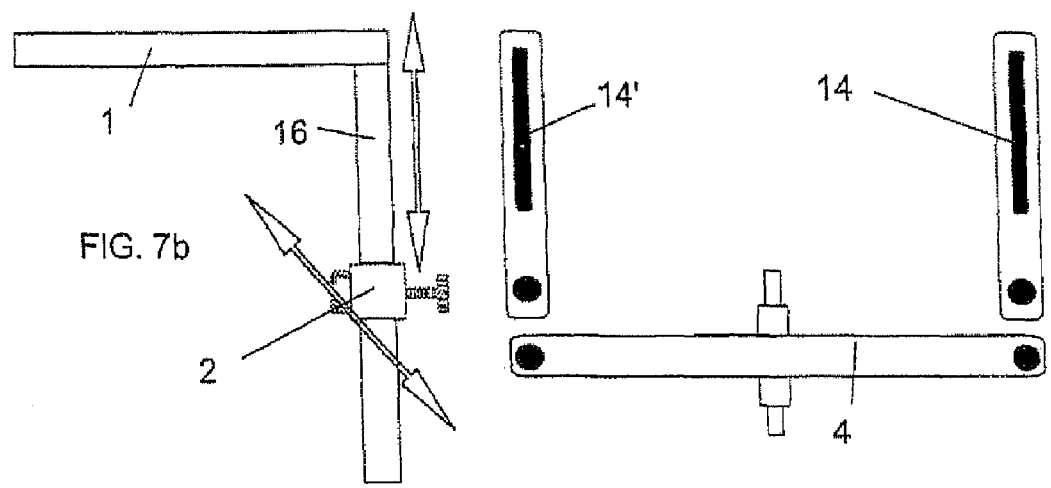
FIG. 7b
FIG. 8
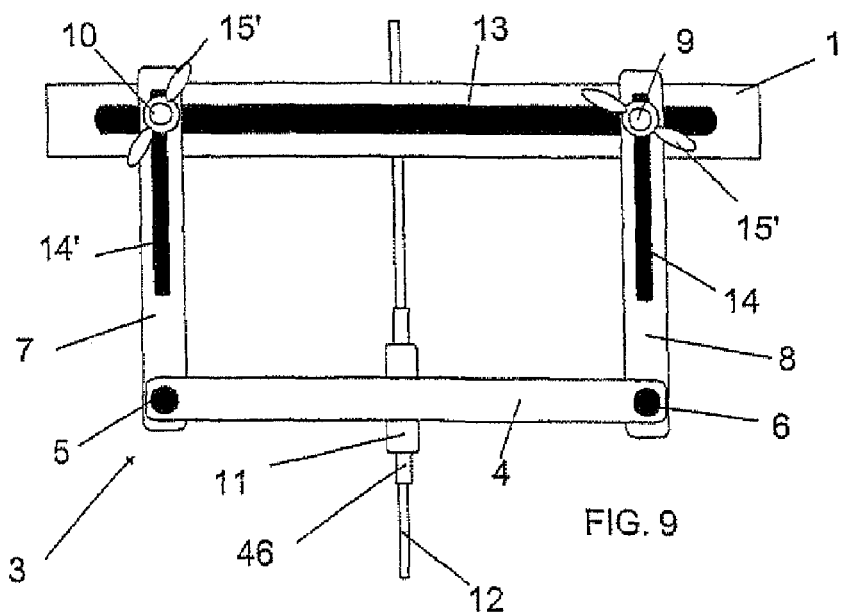
FIG. 9

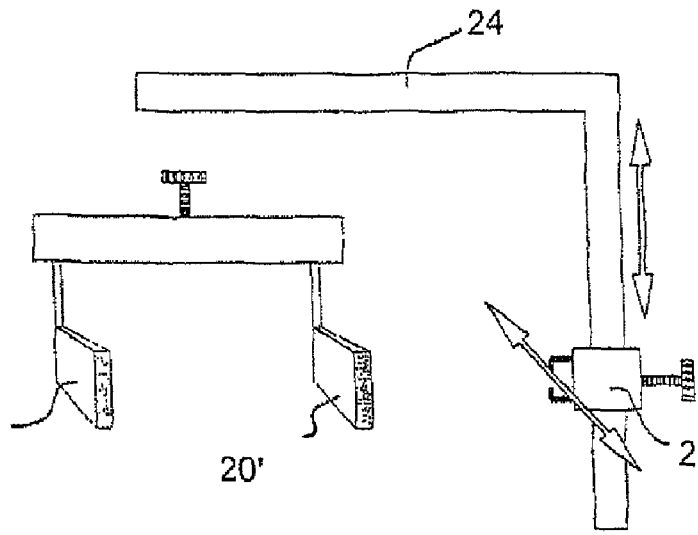
FIG. 25a  20    20'
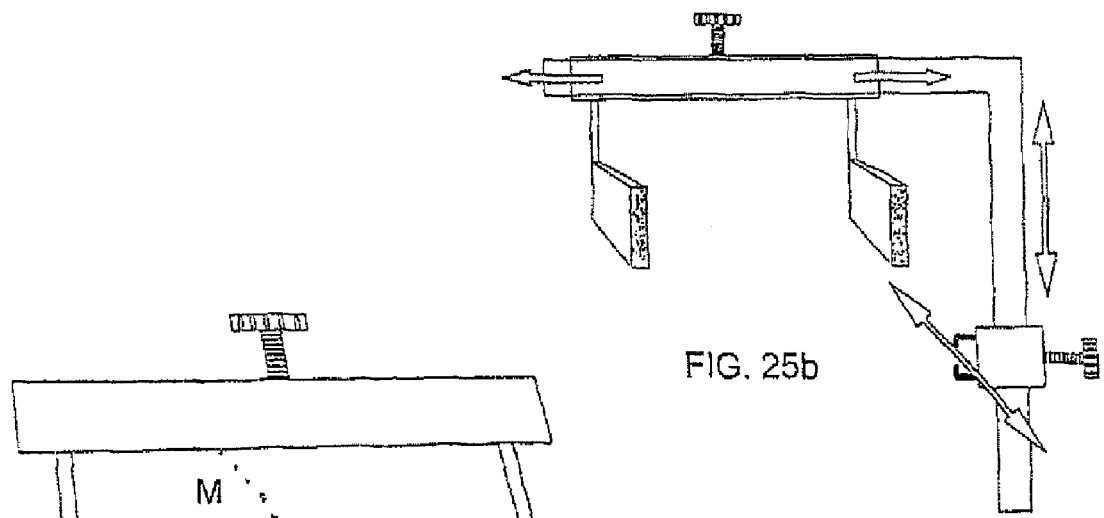
FIG. 25b
FIG. 26

SIGHTING INSTRUMENT FOR DETERMINING THE MECHANICAL AXIS OF THE FEMUR

The present invention mainly refers to a device and to a process that can help to determinate or estimate the orientation of the femoral mechanical axis.

It is a well-known fact that a knee prosthesis has to be placed perpendicularly to the mechanical axis of the inferior limb. This axis goes through the rotational centre of the hip, the centre of the knee and the centre of the ankle.

An arthroplasty of the knee thus requires the realization of bone cutting at the level of the distal part of the femur with the most precise possible orientation.

PRIOR ART

The classical method of achieving this objective consists of measuring on a large pre-surgical radiography of the inferior limb, the angle (alpha) between the diaphysis axis (a) of the femur (real) and the mechanical (virtual) axis (M)).

At the moment of intervention, there is used the femoral diaphysis axis in order to introduce an in-guide rod allowing pulling on the cutting instruments with an angle equal to the alpha angle measured on the pre-surgical radiography.

More recently, "computer assisted navigation" has allowed the possibility of shaping the operated femur and to virtually visualize its mechanical axis in order to adjust the positioning of the prosthesis according to a plan as close as possible to the axis perpendicular to this axis.

The first method, used traditionally for many years, unfortunately lacks precision. In fact, errors of angle measurement on the pre-surgical cliché (rotation errors etc.) can appear. It is also possible to have further degrees of a lack of precision at the moment of the introduction of the metallic rod in the femur diaphysis, in the case that this diaphysis is relatively large and causes a certain freedom in the positioning of the rod. It is not thus uncommon to notice on the post-surgical clichés that the prosthesis has been placed with a larger than three degrees deviation compared to the ideal axis. In addition, the introduction of the rod into the femur diaphysis has some disadvantages, as it destroys, to a certain degree, the diaphysis bone marrow and fat embolisms have been reported in the post-surgical stage, possibly connected to the introduction of this rod.

The second method, computer assisted navigation, seems more precise and the efficiency studies on this method clearly prove that it allows obtaining a significant reduction in the error regarding the degree of positioning of the prosthesis compared to the mechanical axis.

Nevertheless, this method needs, on the one hand, to use sophisticated and costly technical methods and, on the other, in order to put this method into place, it generally entails an increase in the surgical time evaluated between 20 and 30 minutes.

In a more specific manner, the previous techniques can mainly be represented by the following documents:
FR 2 829 376 Bergue Bertrand
U.S. Pat. No. 5,690,638 Dance et al
WO 2004/041097 Aesculap AG & Co. KG
WO 02/47559 Aesculap AG & Co. KG
EP 1 421 042 Zimmer Technology, Inc.
EP 0 839 501 Osteonics Corp
EP 0 677 274 Osteonics Corp The present invention allows determining in a simple fast and less costly manner the exact localization of the mechanical axis compared to the knee and, as a consequence, adjusting, with great precision, the positioning of the prosthesis compared to this axis. It allows, from another point of view, the avoidance of the need to introduce a metallic rod inside the femoral medullar cavity.

General Presentation of the Invention

According to the invention, there is provided generally a device to allow the determination of the mechanical axis of the femur or the direction of the centre of the femoral head relative to the knee.

According to a first aspect of the invention, there is provided a device for the determination of a plane containing the femoral mechanical axis comprising:

a mechanical means of articulated and/or sliding elements in order to determine and memorize two positions in space (F1 and F2) of the same point of the knee (F), freely selected, when the latter is situated in the position P1 and P2, relative to a referential system, the above mentioned positions being obtained by the rotation of the inferior limb from position P1 towards position P2, about the centre of the femur head, a way of materializing the orientation of a plane (omega) passing through the middle of the right segment, defined by the two aforementioned positions F1 and F2, perpendicularly to this segment and containing the centre of the femoral head.

According to another aspect of the invention for memory storage of points F1 and F2, it is foreseen a means of mechanical lock-out of an articulated bar supported by a device provided with at least three degrees of liberty, of which at least one degree for rotation purposes and including at least two ways of locating the aforementioned point of the knee when situated in position F1 and F2.

Preferably, one of the degrees of liberty consists of a vertical or horizontal rotation axis, that is to say perpendicular to the frontal or sagittal plane.

The means of localization can be cylindrical elements, for example hollow, able to be positioned with precision above a fixed localization element at point F of the knee. These means of localization can be drilling guides for inserting or detaching a pin serving as a marker.

Other types of localization, apart from a pin, can be contemplated, for example, using laser marking, or using a pen or a surgery marker.

A method of materializing the orientation is preferably a mechanical method allowing orientating a rod in the middle of, and perpendicular to, the right segment separating the two aforementioned localization means.

A means allowing the disconnection of the aforementioned rod, in order to transfer and fix it onto the femur may also be advantageously provided.

The device can be designed in order to allow the abovementioned rotation in a frontal plane, in a sagittal plane or, preferably, in both planes.

The device is fixed to a referential system that can, for example, be a surgery table or the patient's pelvis, for example at the level of the iliac bone, more specifically of the iliac cavity.

According to another aspect of the invention, there is provided a device for the determination of the direction of the centre (Ct) of the femoral head in relation to the centre of the knee (Cg), comprising:

a mechanical means of articulated rods containing an arm where two points (E1, E2) can be freely immobilized, each in a fixed and constant relative position, at two positions in space (F1 and F2) of the same point, freely selected (F) of the knee when the latter is in two different positions (P1 and P2) in the frontal or sagittal plane.

a means to materialize the direction of a straight line perpendicular to the middle of the aforementioned rods, the aforementioned straight line rod being parallel or contained in the frontal plane (P).

The invention concerns also a method of determination of the mechanical axis of the inferior limb, comprising the following steps:

determination and memory storage, via a mechanical assembly of articulated rods, of two positions (F1, F2) of the same point (F) of the knee, freely selected, relative to a surgery table or the patient's pelvis, the aforementioned positions being obtained by rotation of the hip strictly in the frontal or sagittal plan, about the centre of the hip.

orientation of a rod in the middle and perpendicular to the straight line separating the two aforementioned positions (F1, F2), alignment of the rod with the centre of the knee.

According to one aspect of the invention, the method is characterized by the fact that the mechanical assembly of articulated bars consists in a quadrilateral element attached to the surgery table; where one of the sides of the quadrilateral is, after adjustment, rigidly fixed compared to this table and the opposite side has a length equal to the distance to be determined, that is between points F1 and F2, the ends of the said side and the two other sides being articulated about the two hollow axis.

It will be understood that other options are also possible for arranging the articulated and sliding mechanism in order to reach a similar result.

Thus, according to another embodiments, a system of four articulated rods forming a parallelogram, of the pantograph type, can be advantageously used. One of the angles of the parallelogram, attached to a support structure of the surgery table or the patient's pelvis, is immobilized compared to the chosen and determined referential system, and determines, with a marking means, the point F1 to the position P1 of the knee. The opposite angle can be freely brought by stretching of the structure, in front of position P2 in order to determine F2 with a second marking means. An independent attached mechanical rod, passing through the two other angles will indicate the direction of the femoral head centre. In this system there is no more need to adjust the position of the inferior limb to the position imposed by the instrument. It is, on the contrary, the instrument that will seek the position of F2 by moving one of the angles of the pantograph until it coincides with the position in the space occupied by the bone mark.

According to another solution, one could conceive a bar, having r the shape of an arm, preferably a graded, fixed bar, perpendicular or not to the axis of the surgery table or a pivoting bar comprising a slider provided with a marker means which is activated in order to slide to the end of the arm and to determine point F2 in the position P2 of the knee.

The slider shall move along a section located at the distal end of the arm, preferably comprising a slit which allows the passage of the marker means. The second locating means is fixed onto the bar in order to determine the point F1 in position P1, at the level or not of the swivel if any. A second slider could pass smoothly on the bar and be carried in the centre of the two locating means fastened in a well-known way subsequent to the detection of F1 and F2. Applying the same principle one could resort to a system of telescopic bars, the sliding bar comprising the locating mark means on its end in order to determine F2.

LIST OF FIGURES

The invention will be better understood when reading the description that follows, given only as examples, making reference to the drawings in the annex, in which:

FIG. 1 generally illustrates the mechanical axis of the inferior limb,

FIGS. 2 to 6 describe the geometrical principle on which the invention is based

FIG. 7 describes the fixed support of a device according to the invention

FIG. 8 describes the mobile part forming the sighting system

FIG. 9 shows viewed from above a set of the illustrated device

Figure 12:
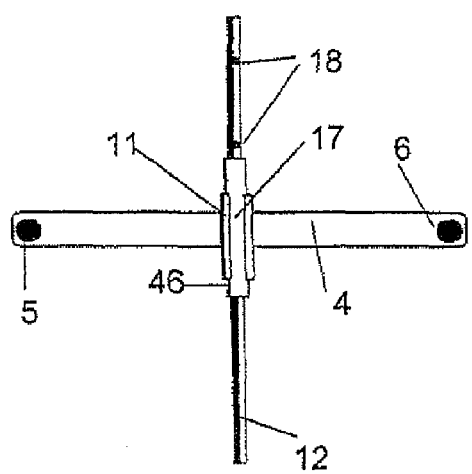

FIG. 12 describes the fixed and mobile support forming a canon

Figure 13:
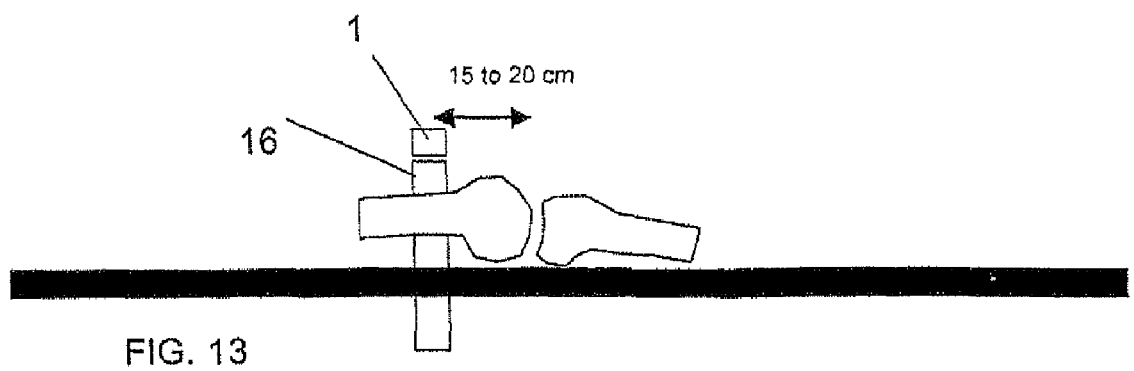
Figure 14:
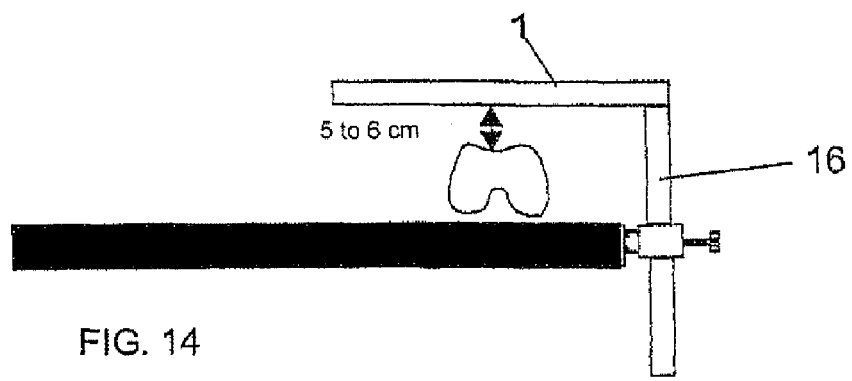
Figure 15:
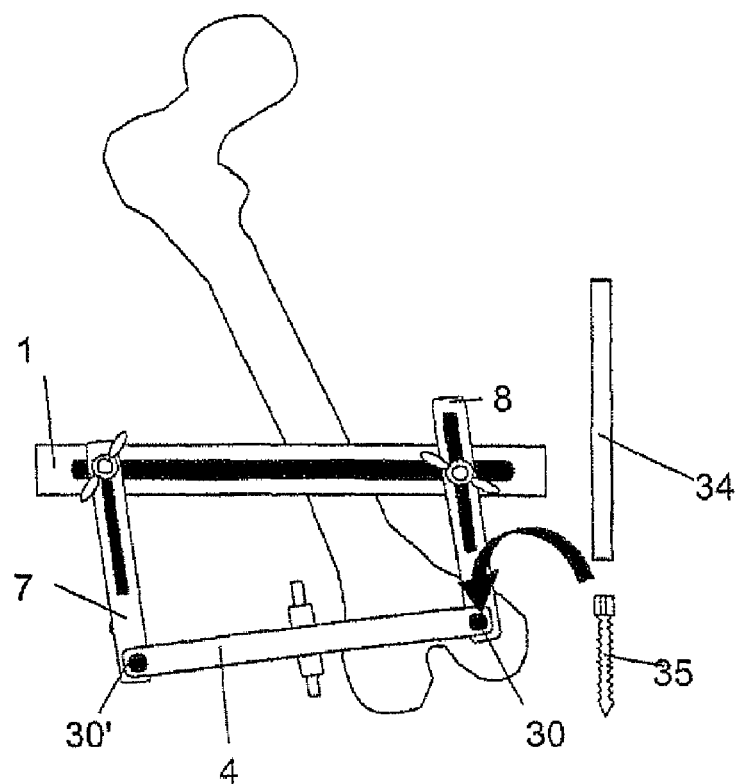
Figure 16:
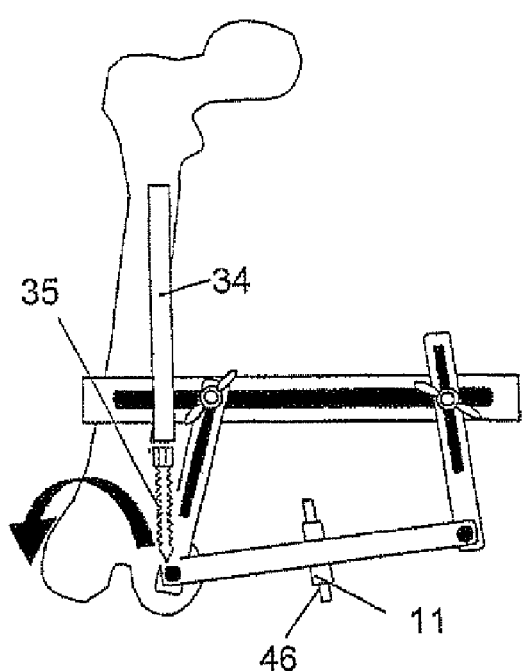
Figure 18:
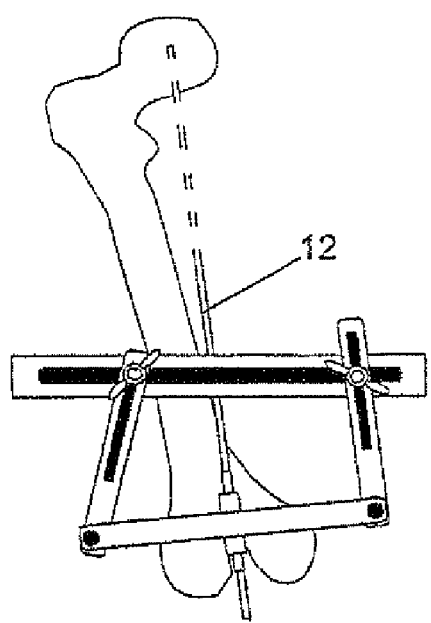
Figure 17:
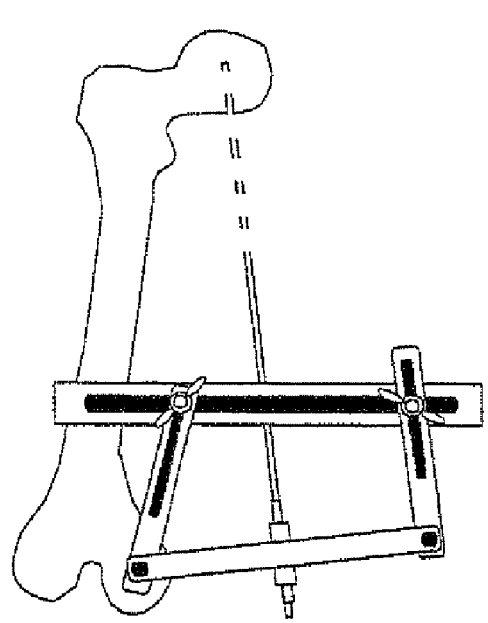
Figure 19:
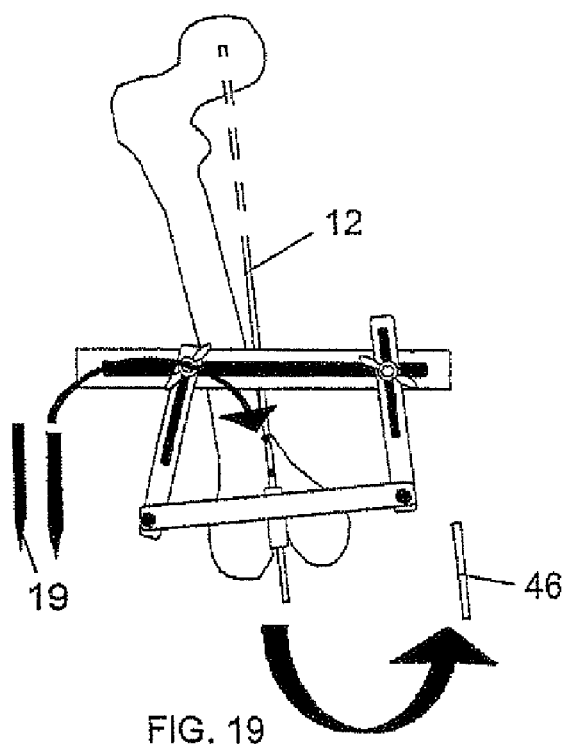

FIGS. 13 and 14 describe the apparatus positioning in relation to the knee

FIGS. 15 to 19 describe the steps for using the apparatus according to the invention.

Figure 20:
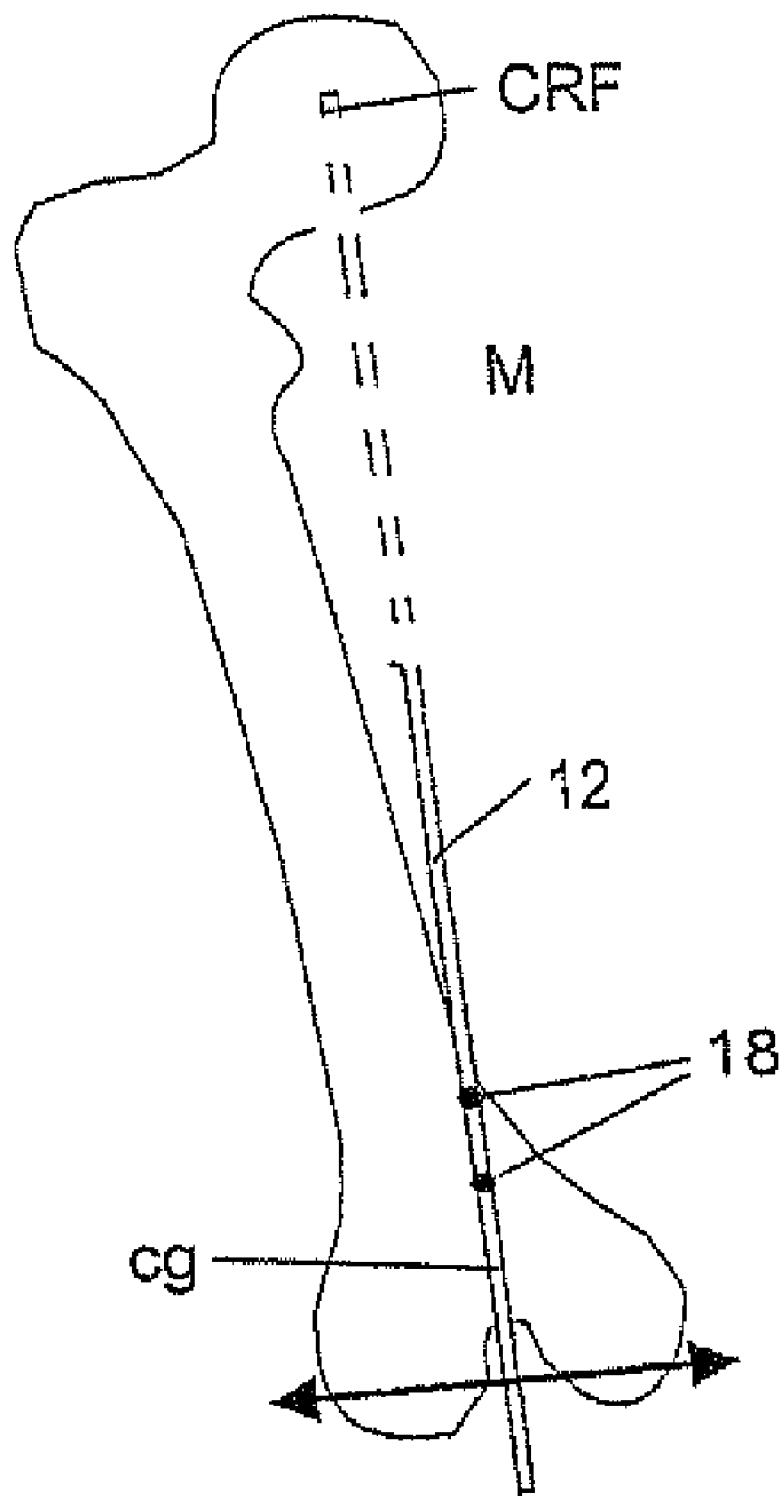
Figures 21, 22, 23, 24:
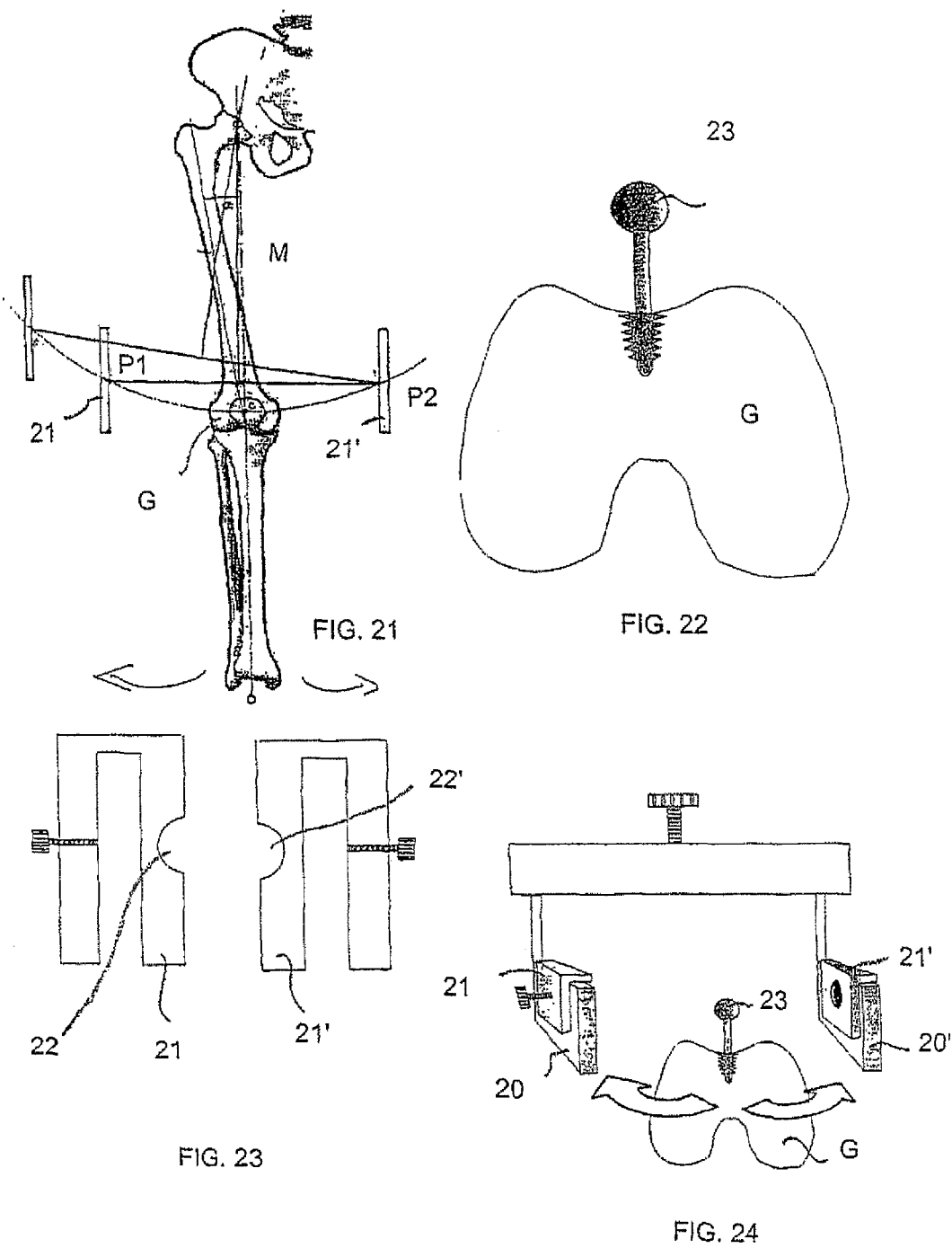
Figure 33:
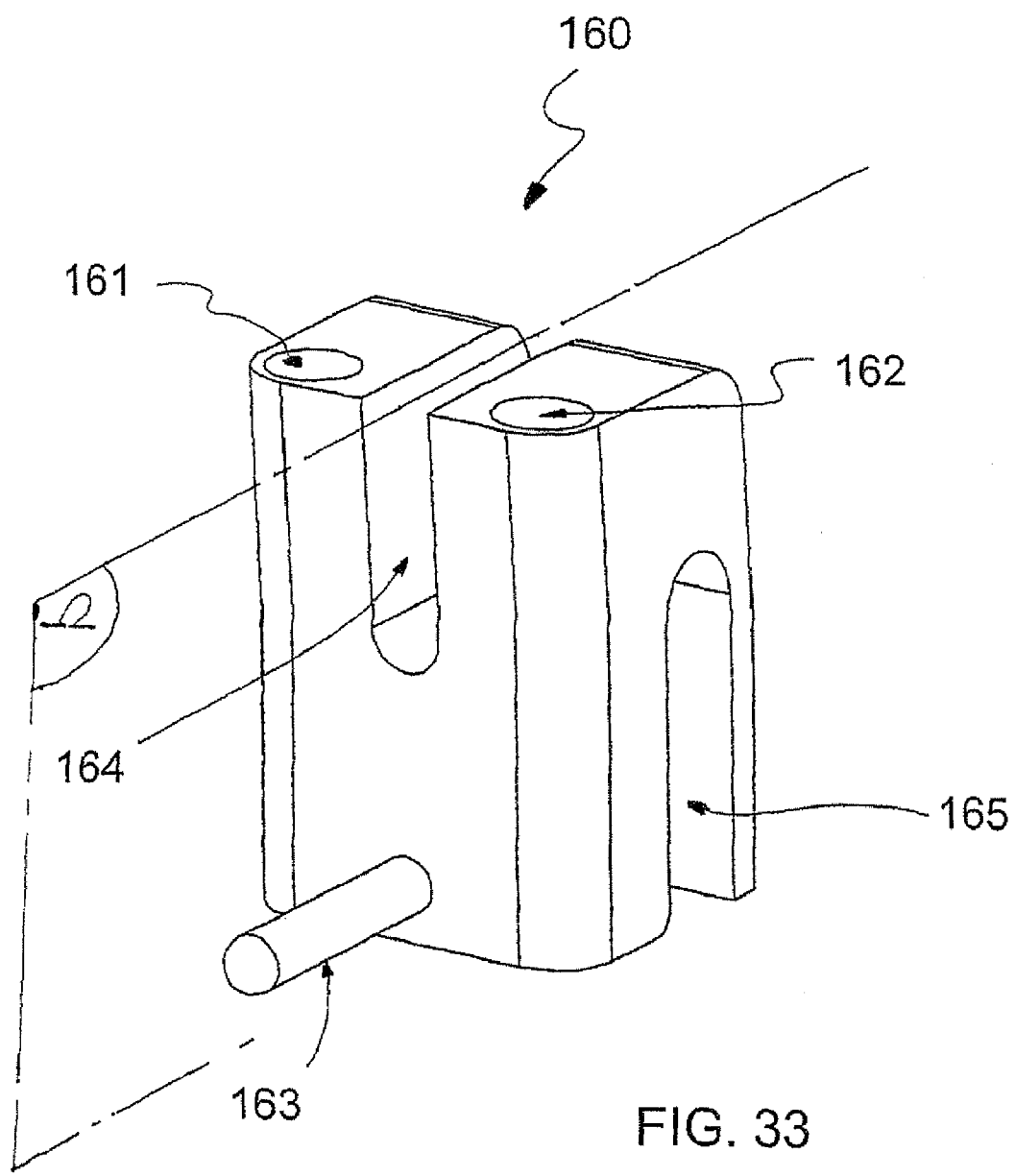
Figure 34:
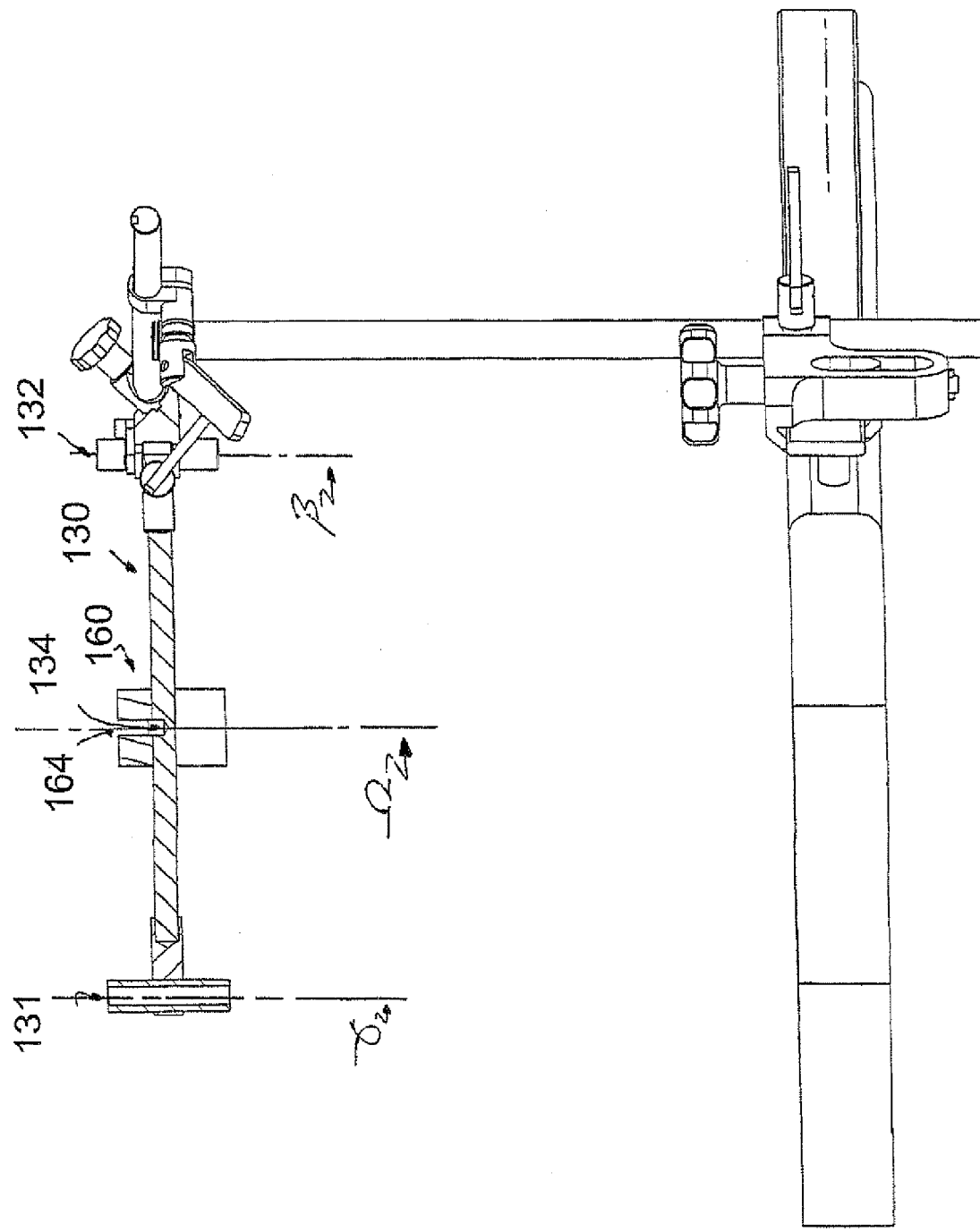

FIG. 20 shows a femur provided with a rod determining the mechanical axis of the inferior limb FIGS. 21 to 26 describe another embodiment of the invention, which is currently less preferred. FIGS. 27 to 42 describe the presently preferred embodiment of the invention FIG. 27 exemplifies in perspective a first assembly of articulated elements fixed to a surgery table FIG. 28 is a side view of the same assembly FIG. 29 exemplifies in detail an adjusting means of the unit FIG. 30 exemplifies in perspective a second assembly of articulated elements designed to cooperate with the first assembly FIG. 31 represents a vertical section passing through the centre of a final adjustment bar of the second assembly FIG. 32 exemplifies an end fitting and threaded spindle cooperating with a guide provided in said final adjustment bar FIG. 33 illustrates a sighting unit fixed on the above mentioned final adjustment bar FIG. 34 represents a section further explaining FIG. 33

Figure 35:
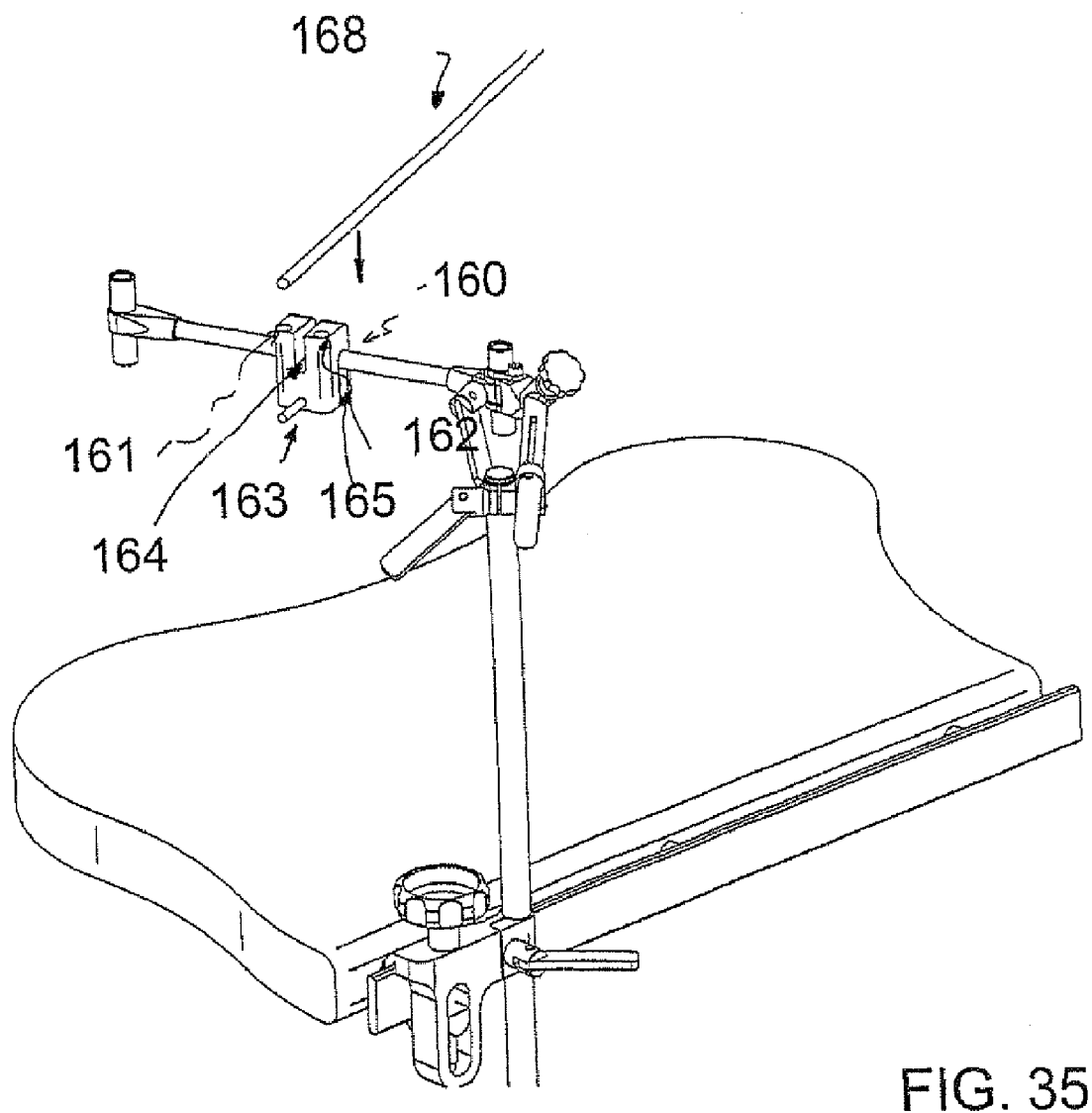
Figure 36:
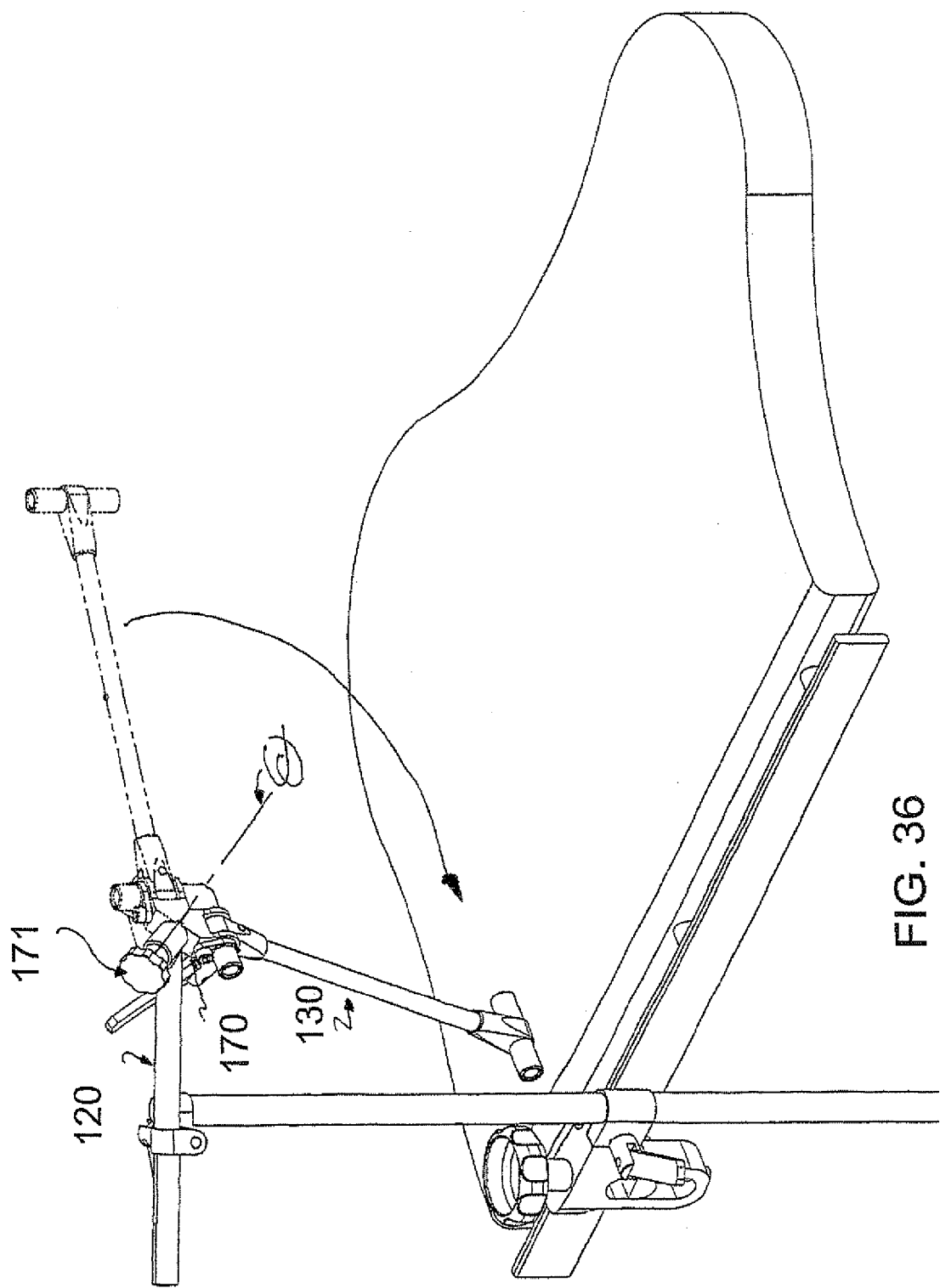
Figure 37:
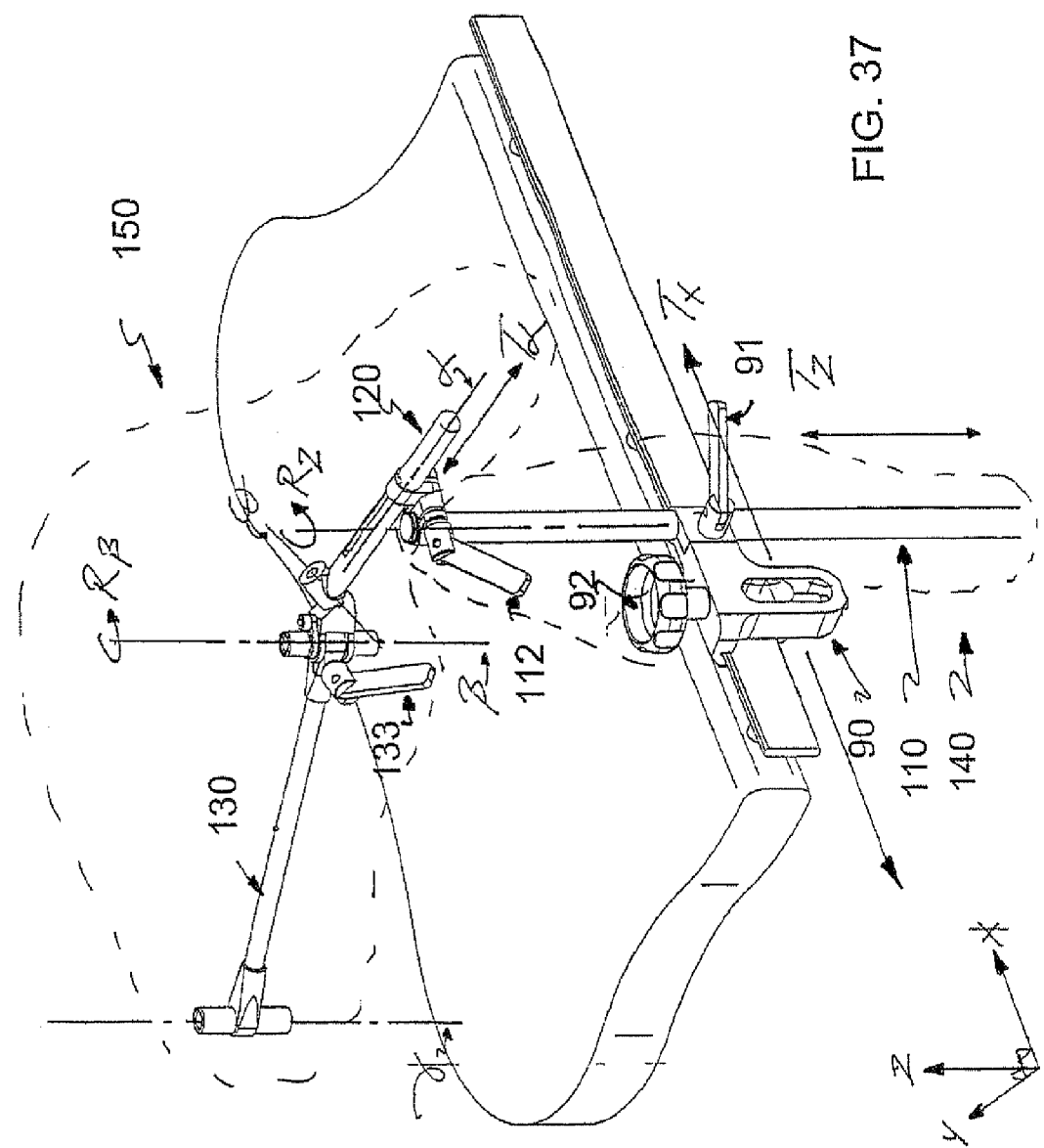
Figure 38:
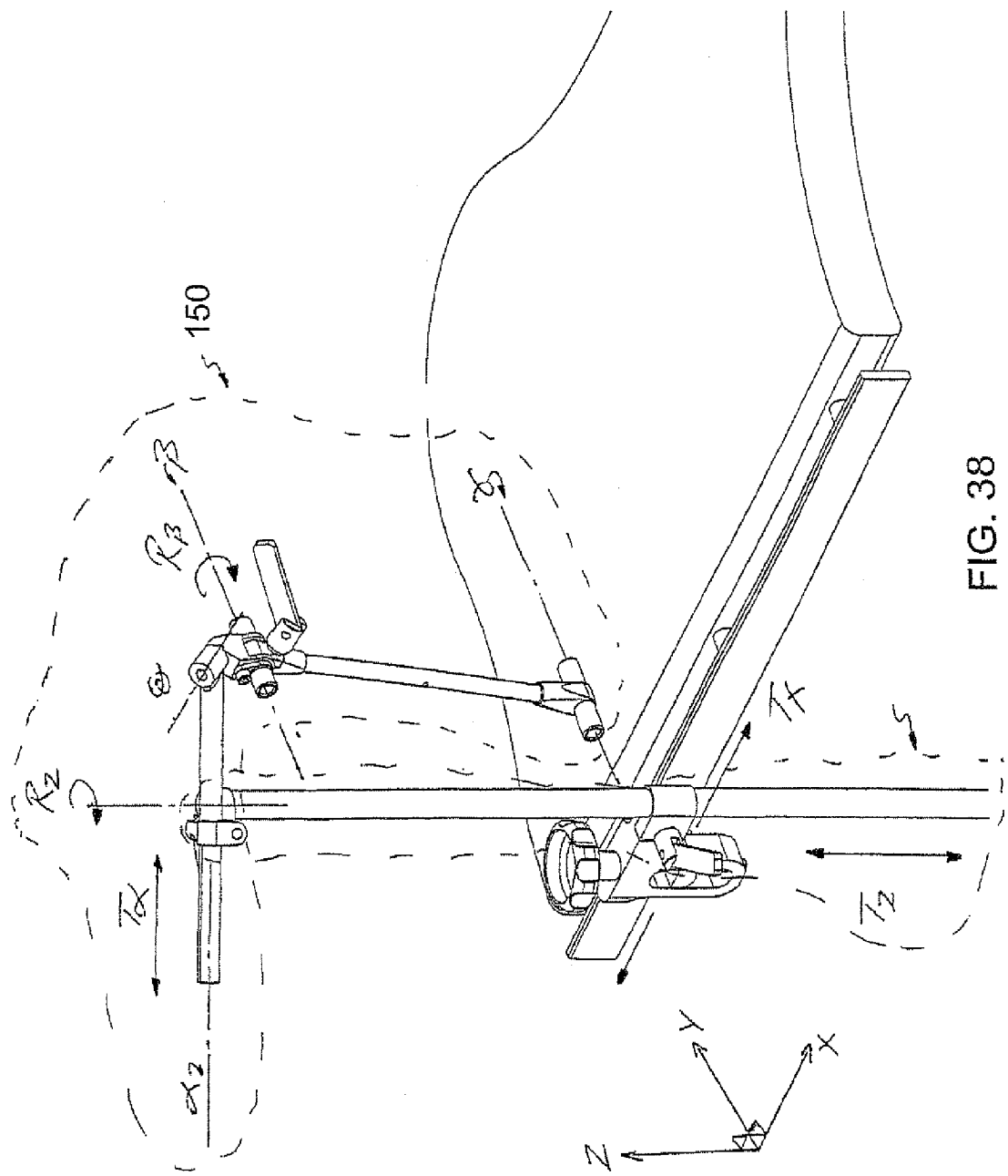
Figure 41:
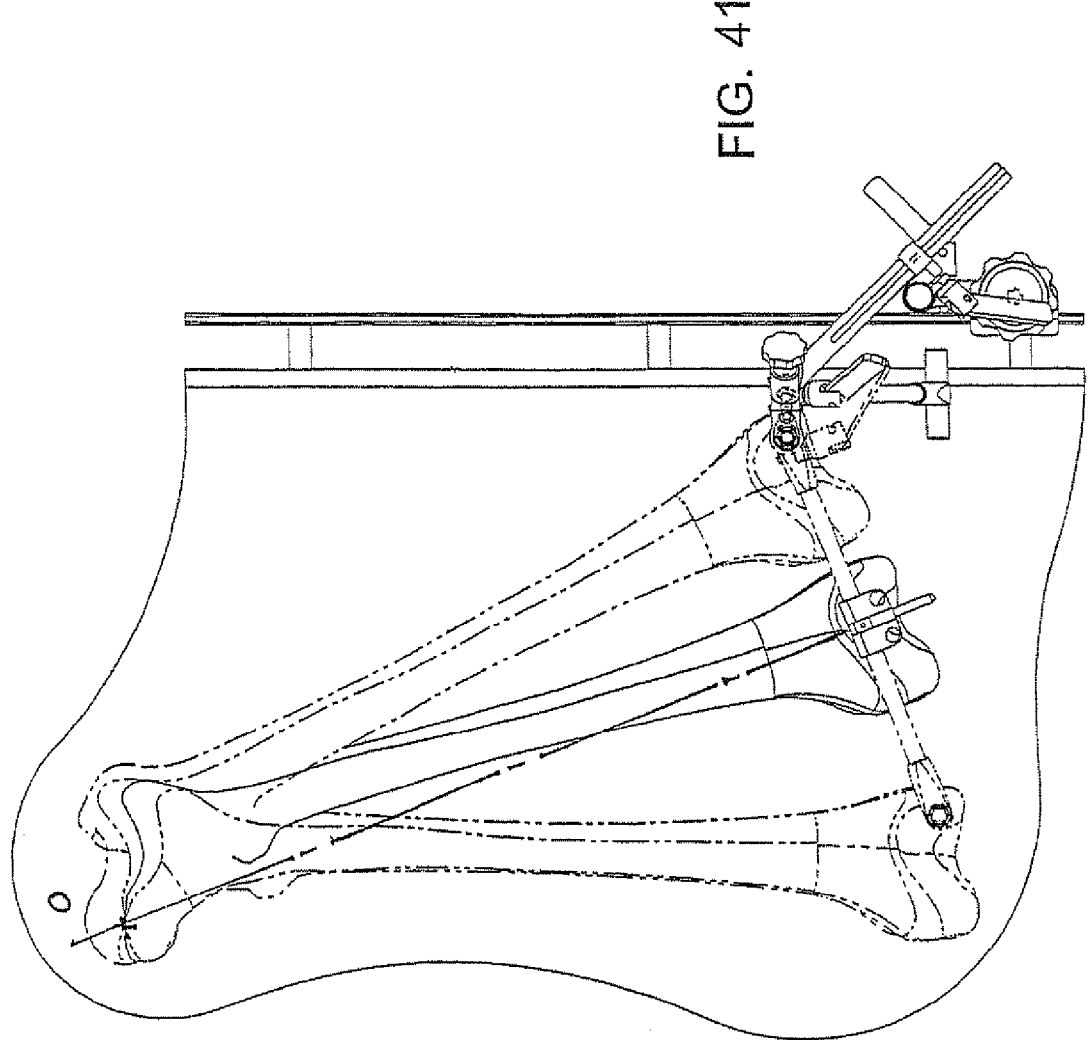
Figure 42:
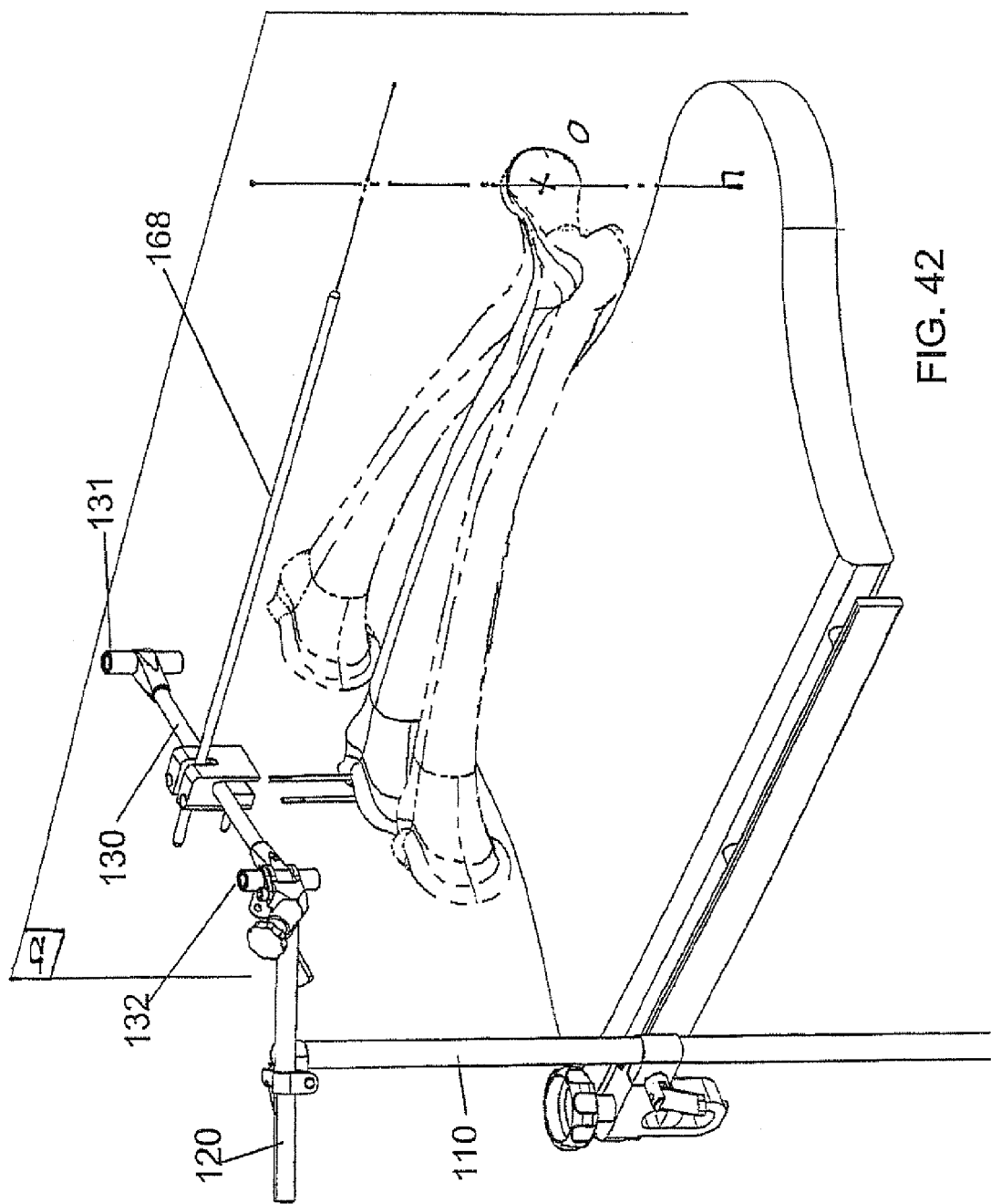
Figure 43:
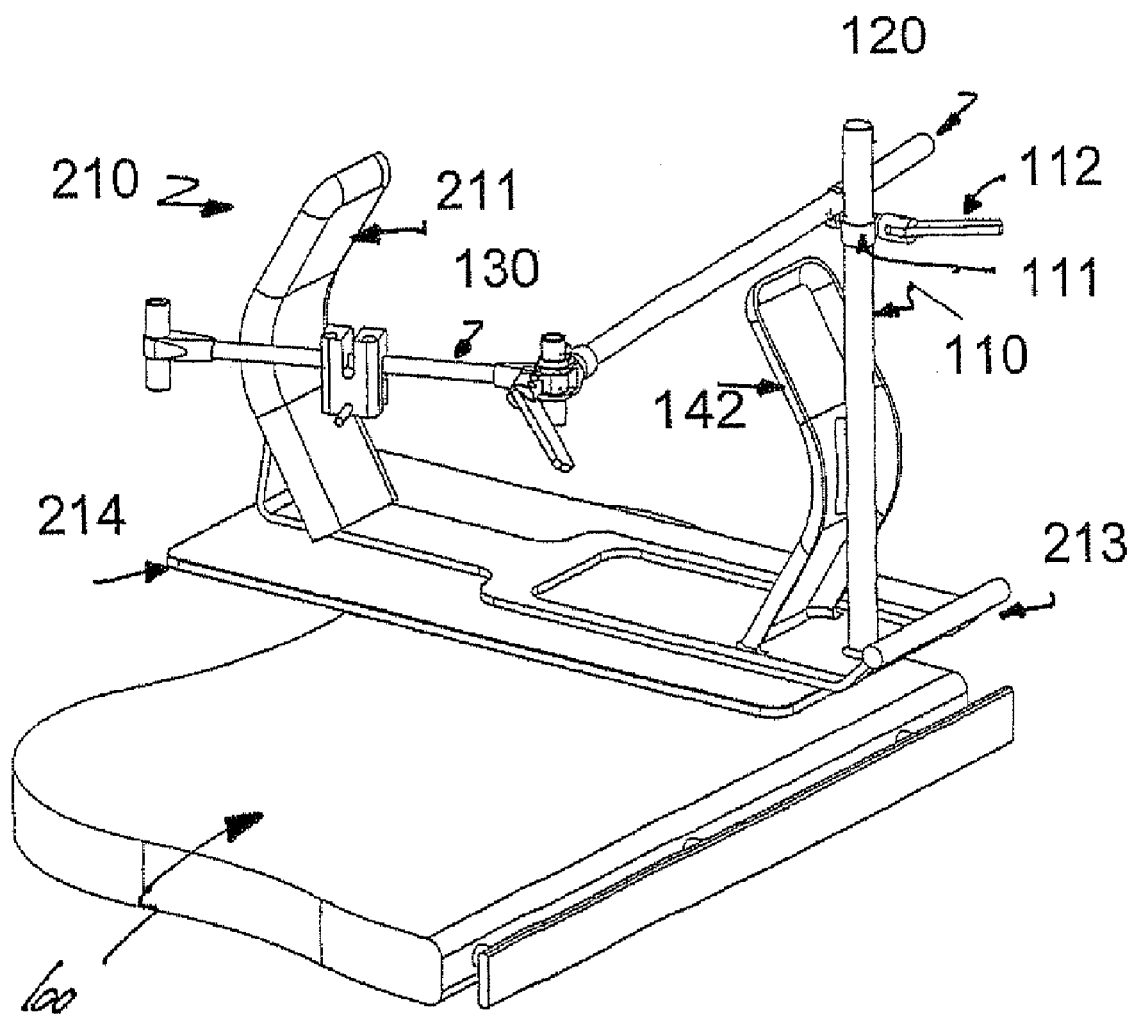
Figure 44:
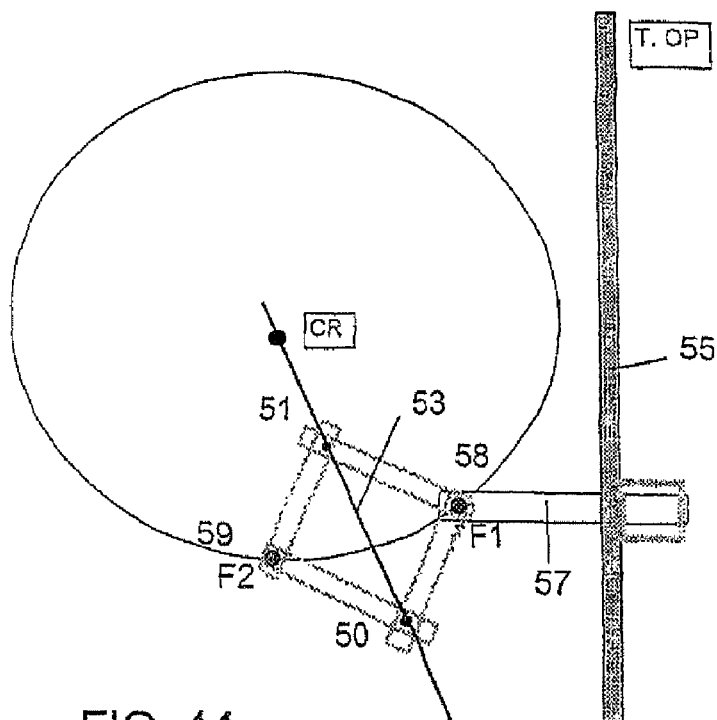
Figure 45:
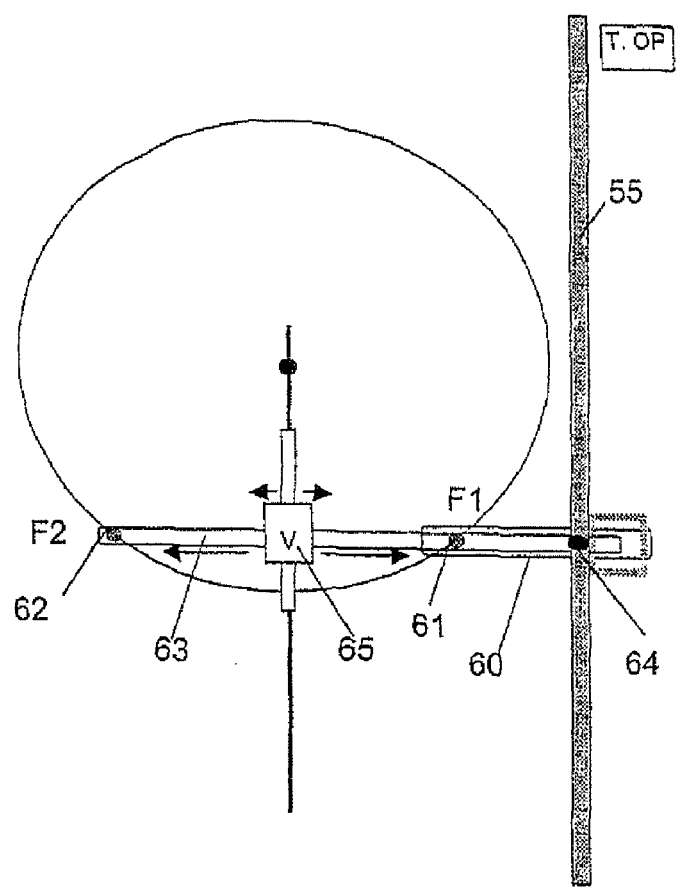

FIG. 35 shows the setting in place of a alignment bar or rod cooperating with the sighting system FIG. 36 explains the configuration shift of the apparatus allowing the measurement to be made from a frontal plane to a sagittal plane FIG. 37 represents a general view of two assemblies of elements operativaly coupled with different indicated degrees of liberty, FIG. 38 represents a corresponding view for adjustments in the sagittal plane FIGS. 39 to 42 illustrate the technique for using the instrument, FIG. 43 refers to an alternative mode of the preferred embodiment wherein the referential system is the pelvis of the patient and no longer the surgery table, FIG. 44 schematically illustrates a particularly advantageous variant of the invention resorting in an articulated quadrangular of the pantograph type FIG. 45 equally exemplifies, schematically, another variant of the invention resorting to a telescopic device.

DISCUSSION OF THE FIGURES

FIGS. 2 to 6 explain the geometric principle on which the invention is based.

Figure 1:
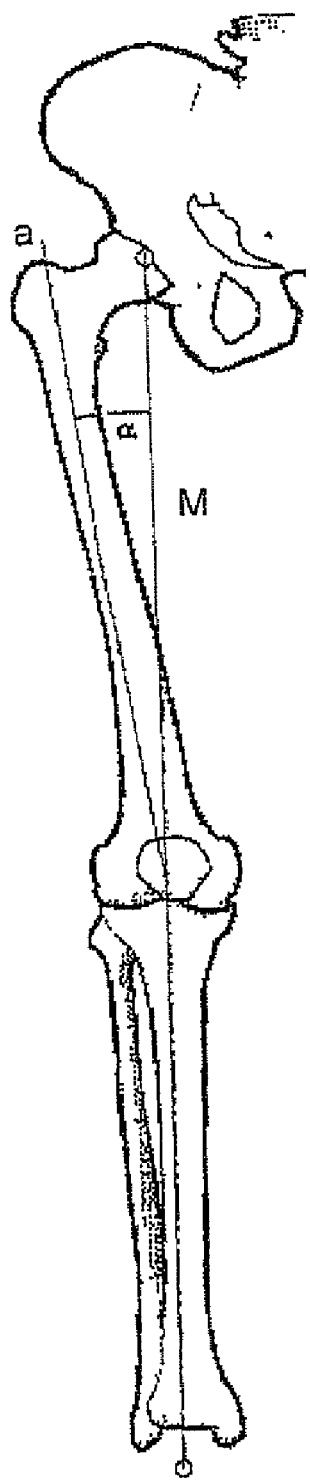
Figure 2:
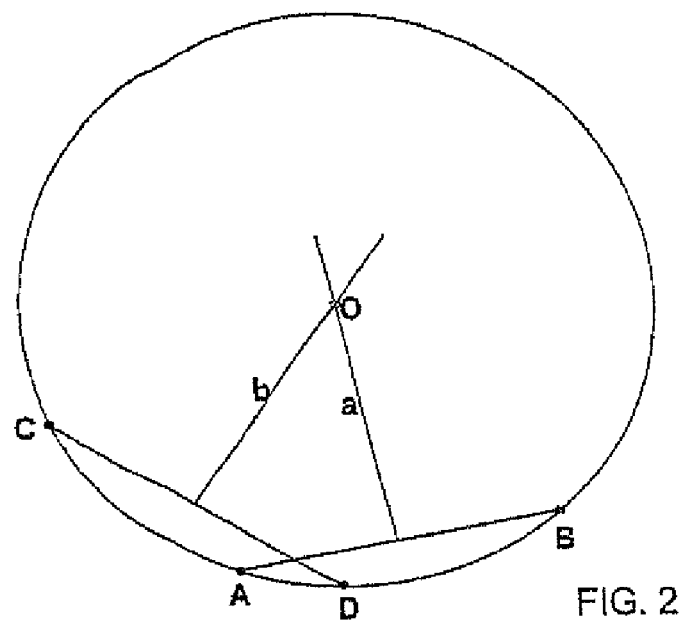

The perpendicular brought down through the middle of the straight line segment joining any two points of a geometric circle, passes through the centre of this circle O (FIG. 2).

For example, the right perpendicular "a" is brought down in the middle of AB passing through the centre O of the circle to whom points A and B belong.

Figure 3:
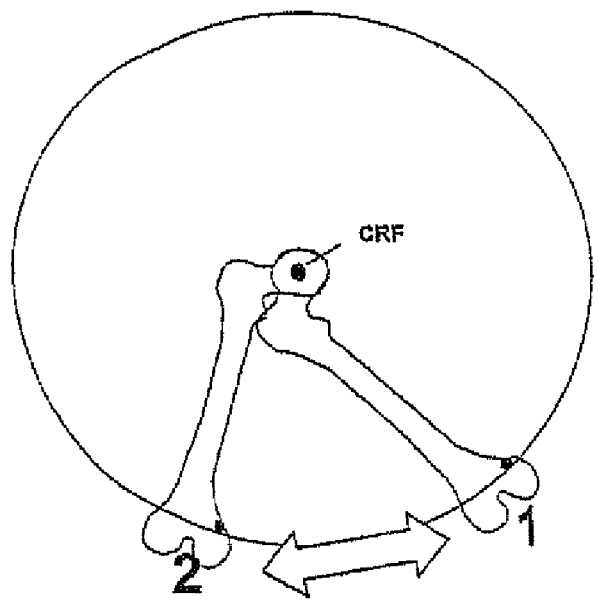
Figure 4:
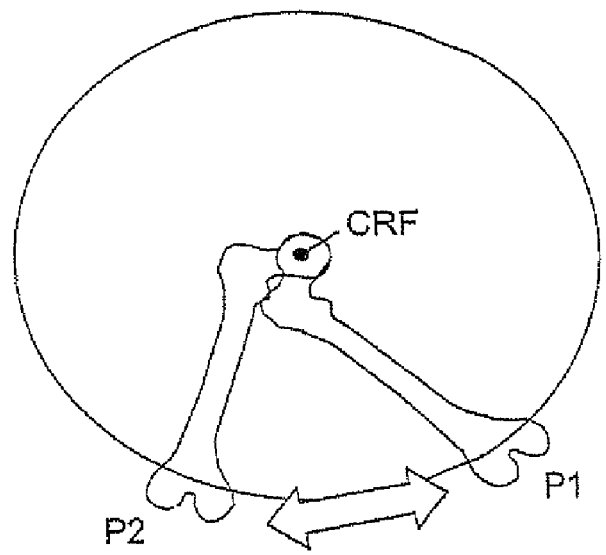

The perpendicular "b" is brought down in the middle of the straight line segment joining two other points, selected at random (C and D) of the same circle also passes through the centre O When the femur pivots in the frontal plane from 1 to position 2 (P2), all points belonging to the femur turn about its rotation centre CRF which resides at the centre of the hip (FIG. 3).

If one marks a certain point of the femur, for example F, and keep it in "memory", the position in space of F when the femur is in position 1, there has been identified the spatial position of F in P1, being F1. One can subsequently locate the position of the same point F of the knee, when the femur is in position 2 and identify the spatial localization of F in P2 being F2.

Figure 5:
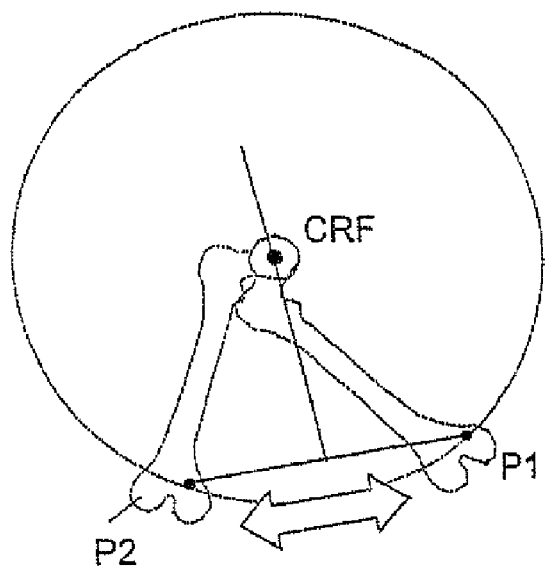

The perpendicular passing through the middle of the straight line segment joining F1 and F2 in a plan containing the centre of the femoral head (frontal plan) crossees by definition the centre of the hip CRF (FIG. 5).

Figure 6:
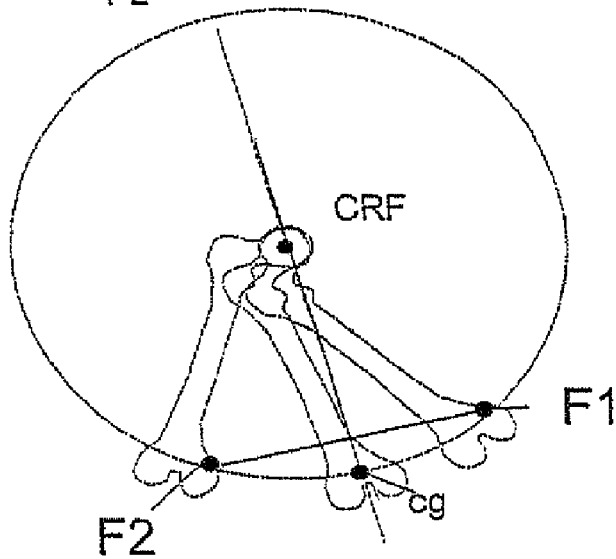

Finally, if we bring the femur into a position such that this perpendicular passes through the centre of the knee Cg, there has been determined the orientation of the mechanical axis of the femur which, by definition, is the straight line joining the centre of the hip to the middle of the knee (FIG. 6).

FIGS. 7 to 9 describe a particular embodiment of the invention in the form of a structure of articulatedbars forming a quadrilateral, composed of a fixed part (fixed support, FIGS. 7a and 7b) and a mobile part (FIG. 8 or sighting system).

FIGS. 7a and 7b illustrate the profile of the fixed part seen from above and from the lateral side.

It is a rigid bar in the form of L containing a vertical segment 16 and a horizontal segment 1. The vertical segment 16 passes in clamp 2, which allows the adjustment of the position of the support according to the afflicted individual. Clamp 2 slides on a metallic rail (not illustrated) fixed along any surgery table. This mechanism allows the adjustment of the position of the L-shaped bar, on the one hand horizontally, in the direction of the head or the feet of the afflicted individual, according to the longitudinal axis of the surgery table and, on the other hand, vertically, in the direction of the ceiling or of the ground of the operating theatre.

Figure 10:
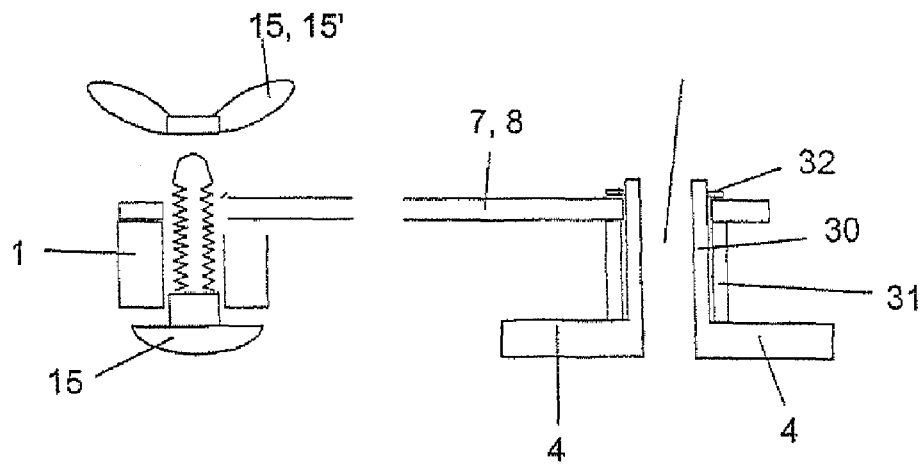
FIG. 10 is a vertical section illustrating an arm with a hollow axis

The horizontal bar 1 is split on its whole length in order to allow the introduction and the sliding of the fastening bolts 15 of the articulated sighting system (FIGS. 9, 10).

The mobile part or sighting system (FIG. 8) contains two mobile arms 7, 8 and a transversal plate 4 that supports the sighting device itself, which is composed of the canon or fixed support 11 and of the mobile canon 46.

The mobile arms 7 and 8 (FIG. 8) are each made up of a metallic plate around 15 cm long, 25 mm in breadth, and 2 of 3 mm thick. Each arm is drilled with a longitudinal slit 14 from 8 to 10 cm long, and 5 to 6 mm in breath (depending on the calibre of the fastening belts) aimed at allowing the introduction and the sliding of fastening bolt 15 connecting the arm 7, 8 to the horizontal bar 1 of the fixed support.

The other end of the plate is drilled with a circular orifice designed to be articulated with the cylindrical swivel located at each end of the transversal plate 4, creating thus, between the two elements a pure rotational movement about axis 5 or 6 passing through the centre of the cylindrical swivel 30 (FIG. 10).

FIG. 9 is a view from above of the sighting system articulated with the horizontal bar 1 of the fixed support.

FIG. 10 represents a vertical section passing through the centre of the mobile arm (7 or 8) on its longitudinal axis.

The transversal plate 4 (FIGS. 8, 9, 10) consists of a metallic plate of around 20 cm long on 25 mm in size, and around 3 mm thick. On its lower side, the aforementioned sighting canon 11 itself is, fixed.

Each of the upper ends of the plate has cylindrical hollow swivel 30 of 2 to 3 cm in height about which the mobile arm 7, 8 is articulated by means of the circular orifice located at its extremity (FIG. 10). Between these two elements there is a cylindrical spacing ring 31 gliding around each cylindrical swivel of the transversal plaque and maintaining the distance between the mobile arm and the transversal plate. This ring 31 has the purpose of bringing down the level of the transversal plate 4 relative to the mobile arm 7, 8 and to the horizontal bar 1 of the fixed support so that the sighting rod 12 of the axis can freely pass under them.

After the articulation of the elements, a stopping system (rivet 32 or other similar mechanism) fixed on the extremity of the cylindrical swivel 30 prevents the pieces from falling apart while, allowing the rotation movement of one relative to the other.

Figure 11:
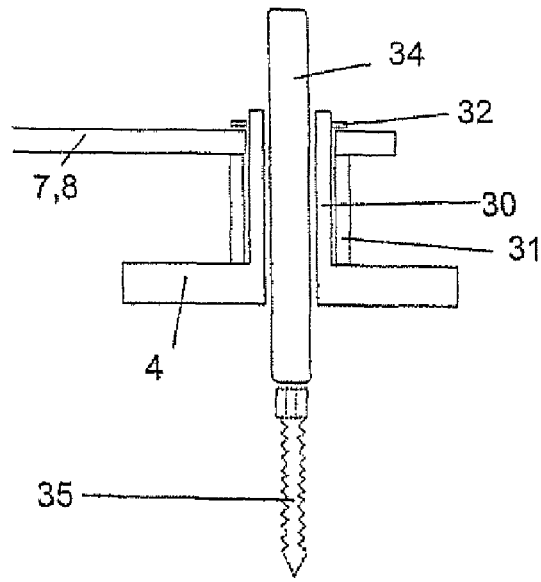
FIG. 11 is a section of the axis with a spindle passing through the hollow part

The interior orifice of the cylindrical swivel 30 is a guide for the introduction of the cylindrical tube 34 carrying the threaded pins 35 which will be introduced into the knee (FIG. 11) at point F. The inside diameter of the cylindrical swivel of the plate will thus be very slightly superior to the outside diameter of the support.

FIG. 12 shows a view, from beneath, of the transversal plate with its sighting canon. This one contains a fixed canon 11 in which a mobile canon 46, and slides which guides the sighting rod 12.

The fixed canon 11 is a metallic cylinder around 3 cm long fixed to the inferior side of the transversal plate 4.

The longitudinal axis of this canon is strictly perpendicular to the long axis of the transversal plate 4 and is to be found exactly in the middle of the distance that separates the central axis of each cylindrical swivel 5, 6.

It is drilled by a longitudinal slit 17, oriented downwards whose length is not enough to let the mobile canon 46 pass but enough to let the sighting rod 12 pass.

The mobile canon 46 is a cylinder 5 to 6 cm long whose exterior diameter is adjusted in order to slide tightly but freely inside the fixed canon 11.

The sighting rod 12 is a rod around 20 cm that slides inside the mobile canon 16. It is drilled by many small holes 18 allowing the introduction of small metallic pins that fix the guiding rod to the femur after having determined its orientation according to the searched mechanical axis.

Its diameter being inferior compared to the length of slit 17 provided in the fixed canon 11, it is sufficient to unblock it to and slide off the mobile canon 46 and the whole device can be taken upwards, in one piece up, by unlocking the fixing clamp 2.

Technique for Using the Instrument

The accommodation is usually performed by dorsal decubitus patient positioning.

One will have to ascertain that the fastening rail provided for the surgery table's accessories is protruding enough in order to allow palpation through sterile field subsequent to their arrangement.

Otherwise, a supplementary rail segment could be fixed to the original rail so that this piece is easily palpated when the surgical fields have been arranged, for easily fastening the sterile jaw vise carrying the fixed support of the instrument.

Subsequent to the setting into place of the sterile areas, the knee is handled using the usual technique.

The knee joint being exposed, the sterile clamp no 2 is prepared and fixed above the surgical areas (while reinforcing them if necessary at the fastening point by a small self-adhesive plastic part).

The positioning of clamp no 2 is adjusted so that the horizontal bar no 1 extends above the patient's knee by around 15 cm cranially (towards the head) compared to the articular interline (horizontal plane) (FIG. 13) and 5 to 6 cm above the knee in the vertical plane (FIG. 14).

In the beginning the two wing nuts 15, 15' (FIG. 9) are unscrewed and the mobile arms 7 and 8 are essentially free to translate and to pivot.

The knee is brought under one of the two cylindrical pivoting pins 30 of the transversal cr bar 4 and the threaded spindle 35 is introduced (motorised) perpendicular in the patient knee G by means of the support 34 guided itself by the circular pin to the horizontal plane of the mobile arm 7 or 8.

The selection of the insertion location of the threaded spindle is entirely free, but once the location has been selected, this location should be vitally "kept in memory".

For this purpose, it is sufficient to clench the wing nut 15 of the mobile arm 14 which was used for the introduction of the spindle 35, before drawing back the spindle support 34.

The clutch of this nut eliminates in fact any free movement of the arm 8 within the space which fix its relative position to F1 and consequently fix the position F1 within the section occupied by the spindle over the arc of circle when the knee finds itself in P1.

Then one brings the knee under the cylindrical pivot of the second mobile arm 7 which is entirely free at that time allowing the easy adjustment of its position in space.

The adjustment is correct when the support-spindle 34 guided by the cylindrical pivot 30 "finds" back the cavity, for instance an hexagonal recess, of the threaded spindle which allows its extraction from the femur.

Before the removal of the spindle-support, it is vital to tighten the second wing nut 15' in order to keep the "memory" of the spindle location in position 2 of the knee (=F2). Thus, determines the spatial location of the second point pertaining to the arc of circle defined by the spindle when the knee finds itself in position P2 (=F2).

The sighting rod 12 is then introduced. By construction, the viewfinder 11 indicates the orientation of the perpendicular passing through the middle of the segment of line and joining the two determined points F1 F2, thus indicating very precisely the direction of the hip's center.

Then one moves the femur until the centre of the knee is exactly placed within the alignment of the sighting rod 12 and consequently, the femoral mechanical axis M has been materialized.

Then the rod 12 can be fastened to the femur by means of tiny nails passing through the holes 18 (FIG. 20) provided alongside the rod (at the same time ensuring that this rod shall remain parallel to the frontal plane).

By removing the mobile canon 46 one the rod is allowed to escape through the longitudinal slit of the fixed canon.

The instrument 3 can be removed upwardly in one piece by simply unscrewing the fastening vise of the support.

The rod determines a perpendicular plane to the frontal plane, also containing the centre of the femur head. The instruments for distal femur cutting will be oriented perpendicularly to this plane which shall facilitate the obtention of a cut strictly perpendicular to the femur mechanical axis. It is to be understood that the orientation in the sagittal plane remains to be evaluated by an identical or complementary technique.

Figures from 21 to 25 schematically illustrate another embodiment of the invention.

The applied principle equally consists in determining two points P1 P2 on the arc of circle defined by the pivoting of the inferior limb in a plane parallel to the body. The bisectrix of the angle formed by this arc of circle shall pass through the rotation centre and brought to the knee, it shall determine the searched axis which will allow a strictly perpendicular cutting of the bone.

The instrument is conceived so that two parallel plates 20, 20', extendon each side of the knee, and are adjustable laterally on a L-shaped support 24 (FIG. 25), fixed to a referential system, such as the surgery table or the patient pelvis and which are slidable towards the head and vertically for instance by means of a vise fastened on the rail of the surgery table. On each of these fixed plates, there is provided a sliding element 21, 21' incorporating an hemispherical hollow 22, 22' facing each other.

These shall constitute contact receptors for a marking member 23 which is quasi-spherical and connected to the knee.

The instrument user guides the rotation of the inferior limb so that the fixed marking member 23 connected to the knee shall touch each of the plates 20. The exact position of P1 and P2 is determined by adjusting the position of the straddling element 21 so that the convex relief of the marking member 23 coincides perfectly with the concave relief corresponding to the hollows 22 of the U element 21, which is then tightened on the plate 20 in order to keep the memory of its spatial position.

The bisectrix of the arc of circle thus determined can be materialized by a mechanical means such as a pantograph 25 provided with a rod 12 forming a bisectrix and provided with 2 spherical sensing elements allowing finding precisely the spatial position of hollows 22 of members 21.

It is understood that various alternatives exist for guiding and fixing an arm or an articulated system by means of two locating means capable to align themselves on a knee marking point in two positions, and thus to materialize a plane passing through the centre of the femur head, for example with the help of a perpendicular rod fixed at equal distance of said both locating means.

DETAILED DESCRIPTION OF A PREFERRED METHOD OF USE

FIGS. 27 to 42 describe in a more detailed way the means of using the invention in the form of a construction of articulated bars 140 and 150 and of a sighting system 160.

For the sake of simplicity, it is considered that the main axis of the patient's body is aligned with the main axis of the surgery table 100 and the surgery table is strictly horizontal (or parallel relative to the ground). Thus, "vertical" means perpendicular to the surgery table and thus to the ground in the present case.

Figure 27:
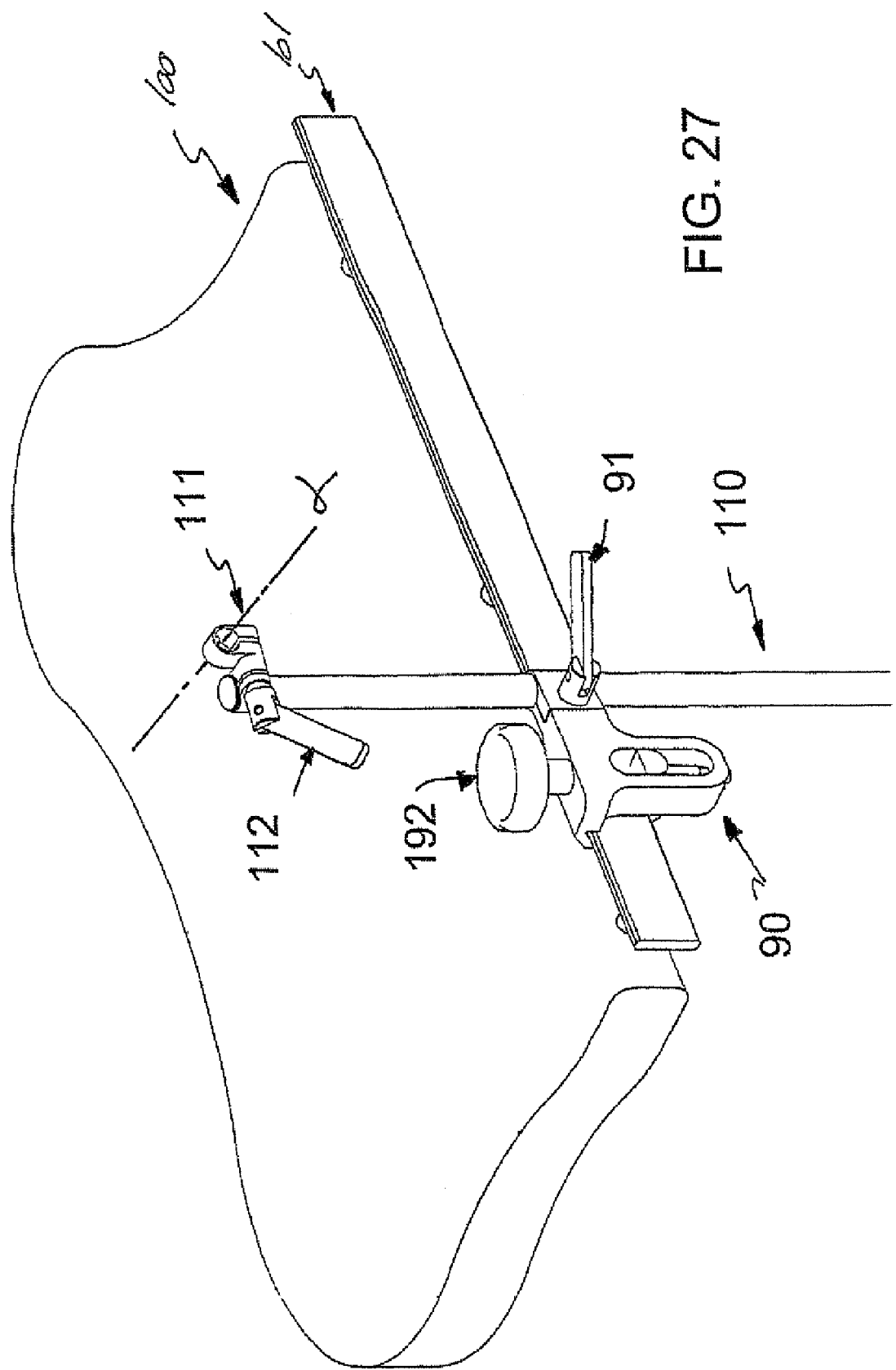
Figure 28:
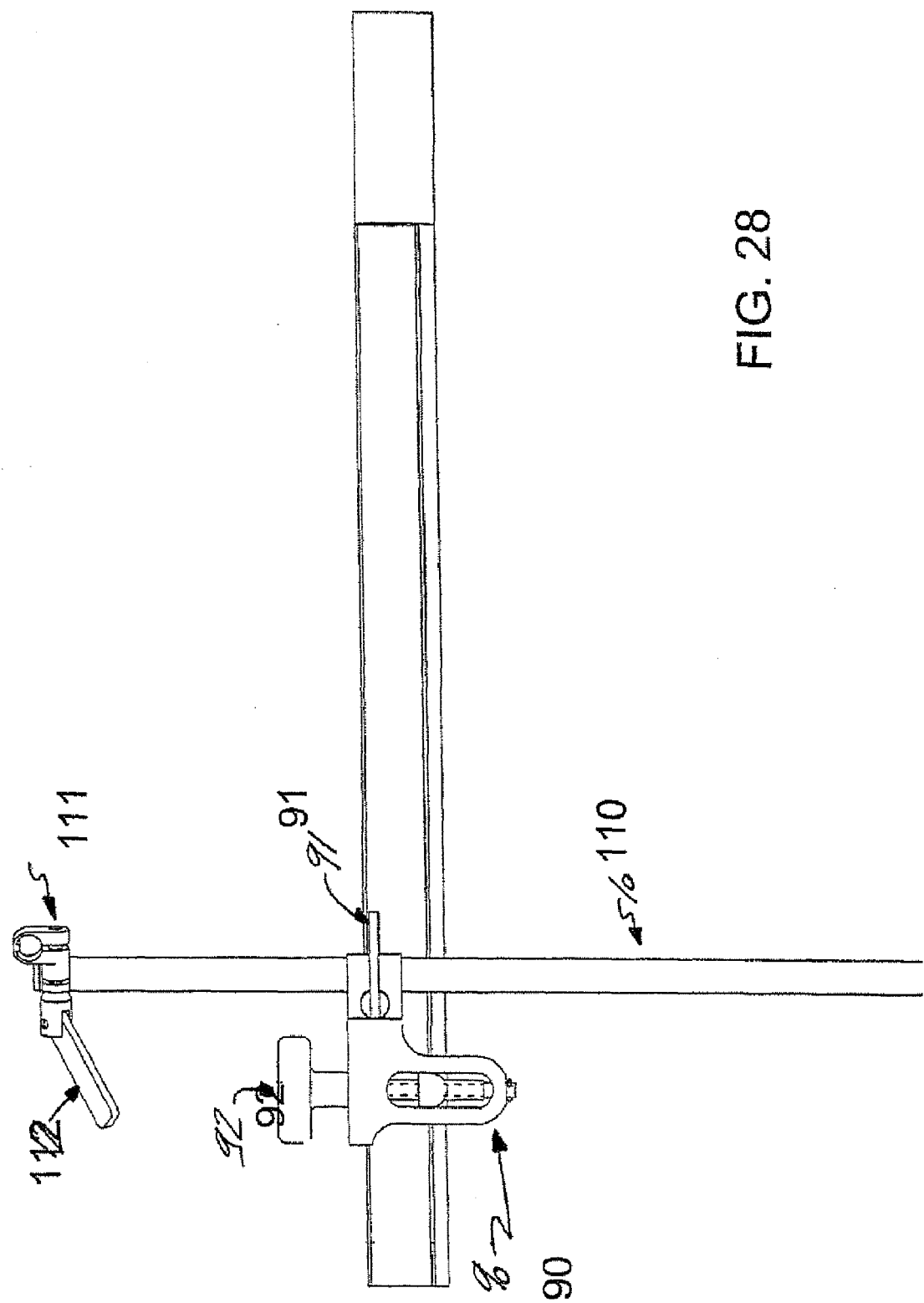

FIG. 27 illustrates the primary adjustment unit 140 made up of a vertical bar 110 and a clamp 190, in a isometric view.

It is a rigid bar 110 being able to slide along the vertical axis (perpendicular relative to the surgery table or perpendicular to the ground considering the surgery table is strictly horizontal) in a vise assembly 90 that allows to adjust the position of the support relatively to the patient. Vise assembly 90 has a 91 that allows the blocking of the vertical translation of the bar 110 in a determined position compared to the clamp 90. In addition, the clamp 90 can be translated horizontally compared to the longitudinal rail 101 of a surgery table 100 meant to receive the patient at the moment of the surgery intervention Vise assembly 90 has a lever 92 that allows to lock the horizontal translation of the vise assembly 90 relative to the table 100.

FIG. 28 is a side view of the same primary adjustment unit 140. The rigid bar 110 can be hollow in order to decrease its weight, it can be made of materials known for surgery instruments' manufacture, such as stainless steel but can also be made of carbon fiber, which allows to combine rigidity and lightness.

At the upper end of the rigid bar 110 there is a guide 111 able to freely rotate about bar 110. The guide 111 is characterized by an opening 113 preferably cylindrical, whose major axis (alpha) is perpendicular relative to the rigid bar 110. The opening 113 is provided with a tenon 114. A clamping lever 112 allows the simultaneous blocking of the rotation of guide 111 relative to the rigid bar 110 and also the adjustment of the opening 113. This will be better understood after the explanations for the use of the instrument (FIG. 29).

Figure 29:
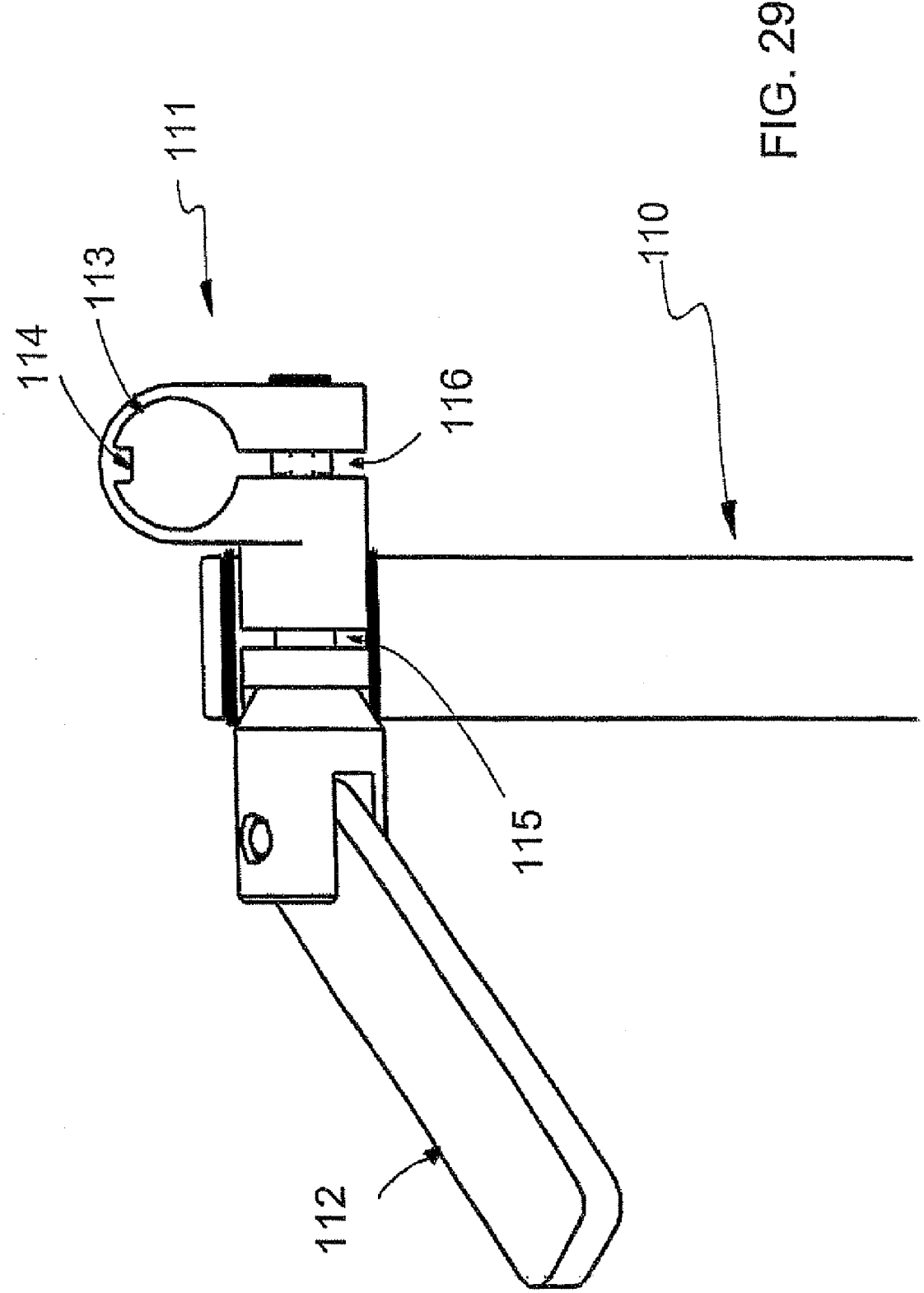

FIG. 29 shows the functioning principle of the clamping lever 112. The guide 111 operates as a clamping flange and is provided with two openings 115, 116. By pivoting the clamping lever 112, the spaces 115, 116 are restrained thus blocking the degrees of freedom given by the support 111.

Figure 30:
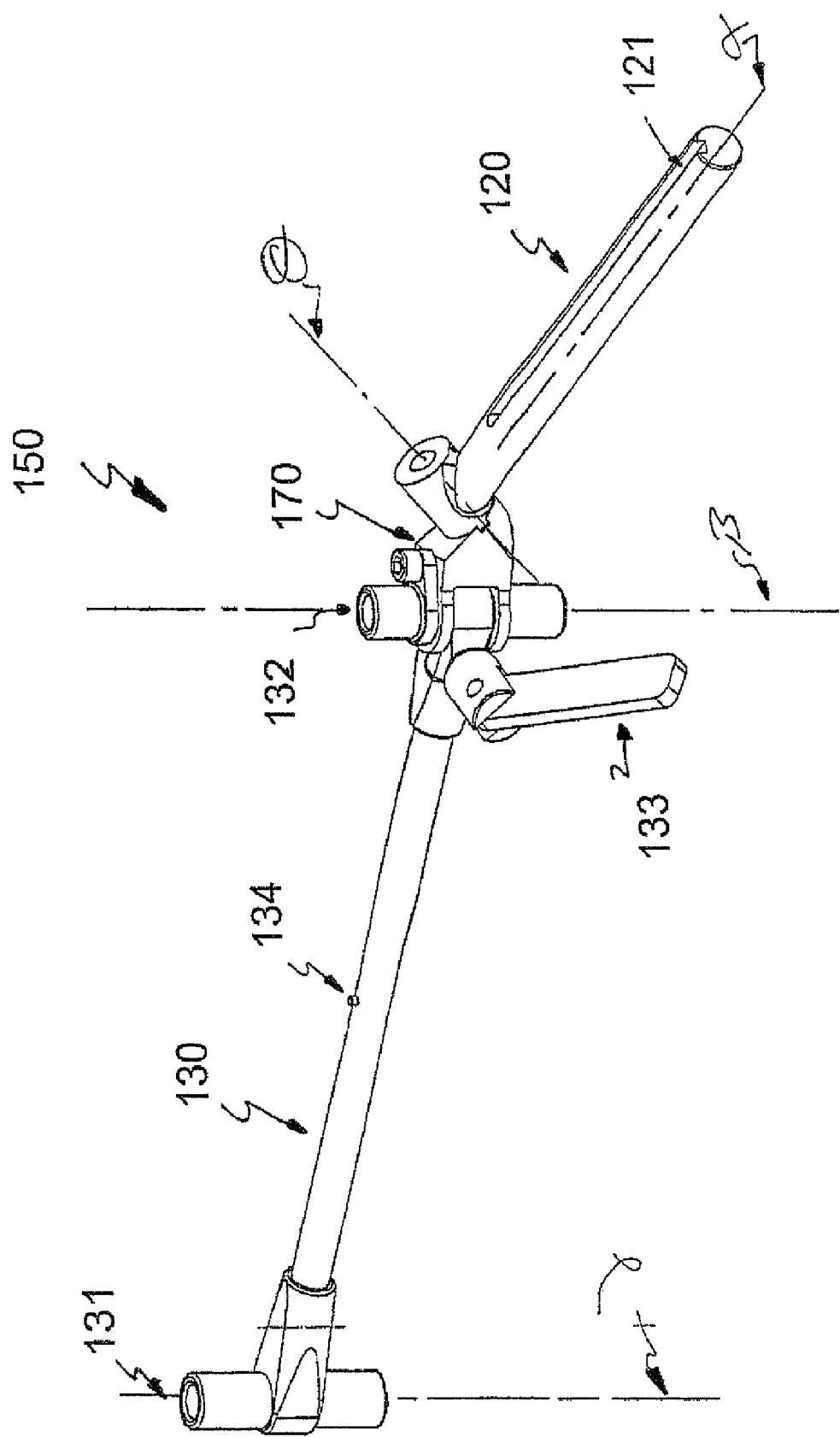
Figure 31:
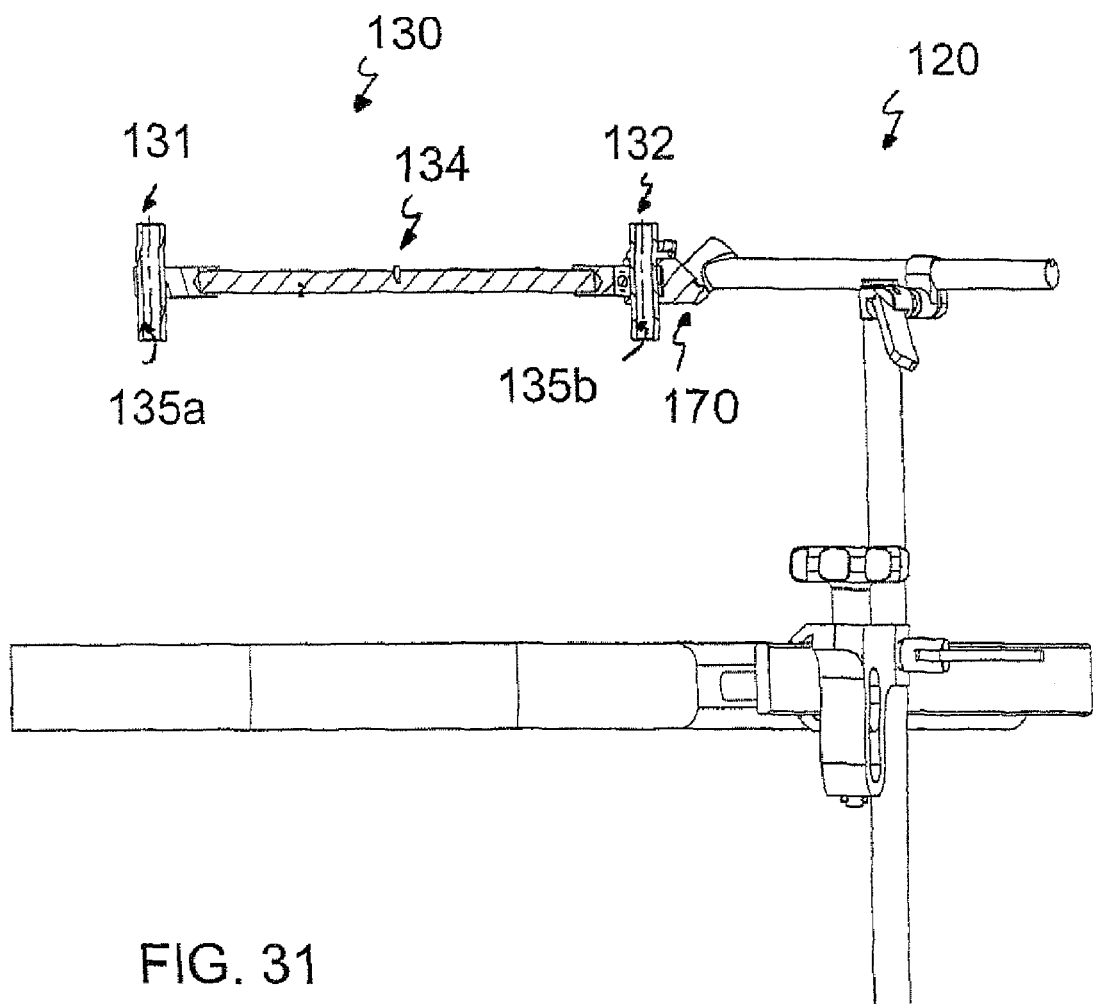

FIG. 30 is an isometric view illustrating the secondary adjustment unit 150 made up of two rigid bars 120 and 130 and an angular transmission 170. The bar 120 has a transverse section compatible with the opening 113 of the guide 111. Along a major part of the bar 120 there is a slit 121 emerging at an extremity of dimension compatible with tenon 114. When it is put together, the set of secondary adjustment 150 is aligned with the opening 113 of the guide 111. The rotation of the set of secondary adjustment 150 relative to the major axis (alpha) of the guide 111 is limited by tenon 114 compared to the slit 121. At the opposite end of the emerging slit, the bar 120 is connected to an angular transmission 170 which allows to change the orientation of the final adjustment bar 130 from the frontal plane to the sagittal plane and reciprocally, according to the decided working plane. The angular transmission 170 integrates a drilling guide 132. The final adjustment bar 130 can rotate about the revolution axis (Beta) of the drilling guide 132. A clamping lever 133 allows the blocking of the final adjustment bars' rotation 130 compared to the adjustment bar 120.

At its opposite end, the final adjustment bar 130 integrates a second guide 131 of dimensions similar to the ones of the guide 132. The revolution axis (gamma) of the drilling guide 131 is parallel to the revolution axis (Bêta) of the drilling guide 132. A locating tenon 134 is fixed together to the final adjustment bar 130 and is located exactly in the middle of the segment that separates the revolution axis (Bêta, Gamma) of the guides 131, 132.

FIG. 31 shows the vertical section (cv) passing through the centre of the final adjustment bar 130 according to its longitudinal axis. Each of the ends of the final adjustment bar 130 provided with a drilling support 131, 132 in the form of a hollow cylindrical swivel, at least 20 mm long.

Figure 32:
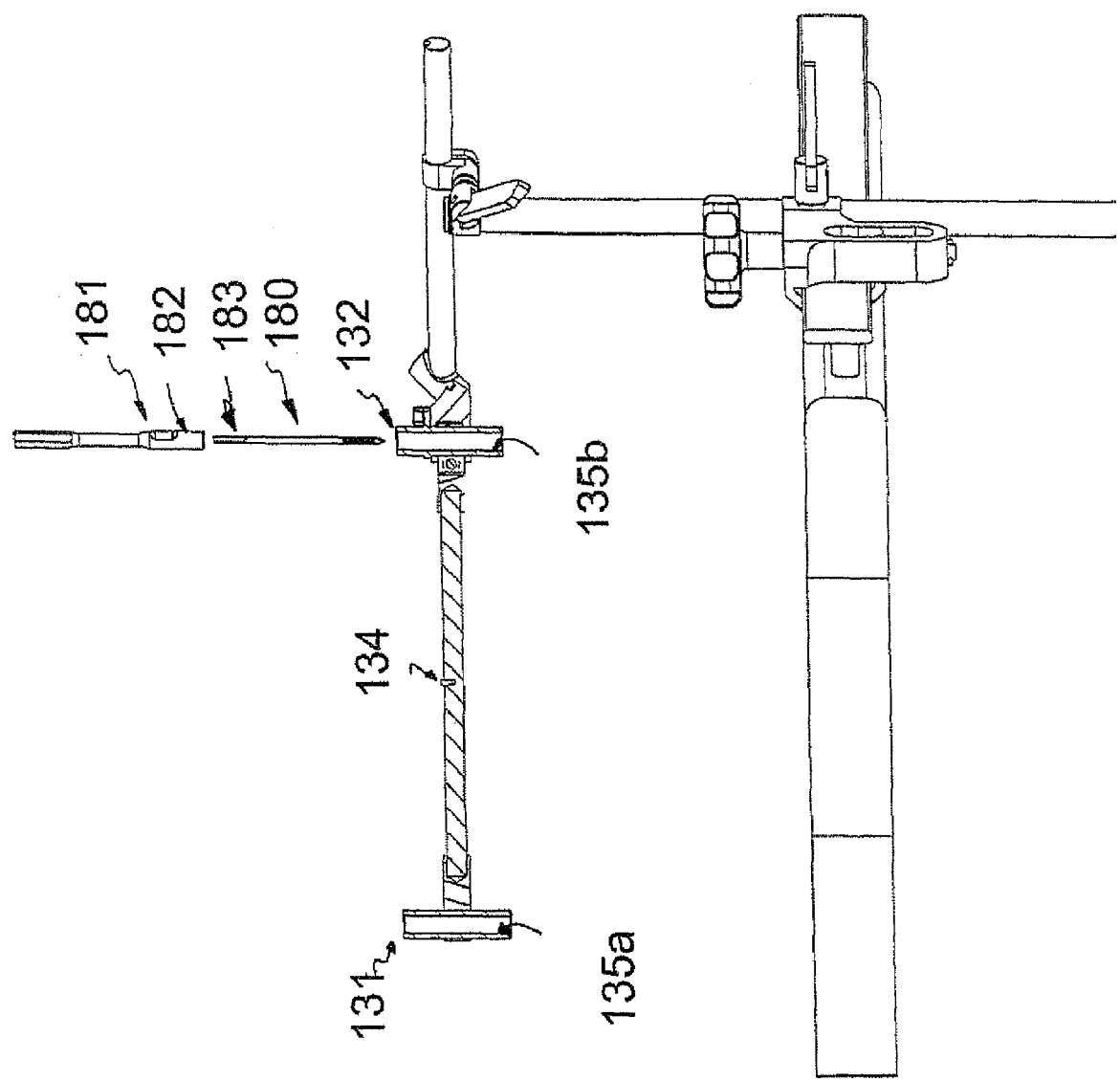

FIG. 32 shows a vertical section identical to the one in FIG. 31. The interior orifice 135a, 135b of the drilling supports 131, 132 is a guide for the introduction of the end fittings 181, within a cylinder 182, carrying a threaded pin 180 which will be introduced in the knee as mark. One should understand that the diameter of the cylindrical carrier 182 of the pin 181 is compatible with the diameter of the interior orifice 135a, 135b of the drilling guides 131, 132. By compatible, it should be understood that the external diameter of the cylindrical seat 182 of the spindle support 181 is slightly under-dimensioned compared to the diameter of the internal opening 135a, 135 but sufficiently close so that the drilling guides 131, 132 shall provide an appropriate guide of the support-spindle 182. For example when the threaded pin 180 is introduced in the knee through the drilling support 132, its implementation axis is the same that the axis Beta of the drilling guide 132.

FIG. 33 is an isometric view of the sighting unit 160. According to an embodiment, the sighting unit 160 of parallelepipedic shape is provided with a first inverted U shaped slit 165 when the unit is ready to be assembled on the final adjusting rod 130 and with a second slit 164, U-shaped, perpendicular to the first slit.

The second slit 164 defines a symmetry plane Omega, where on one and on the other side and at equal distance there are two emerging internal orifices 161, 162 of similar diameter and calibrated in order to receive a threaded spindle (not illustrated). The emergent internal orifices 161, 162 are at a constant distance to the first slit 165, this meaning that a plane created by the revolution axis of the two internal orifices will be parallel to the first slit 165. The first slit 165 and the second 164 are long enough to emerge freely one inside the other. Finally, in the middle of the distal face parallel to the first slit 165 there is a cylindrical tenon 163 long enough to be aligned with the centre of the patient's centre of the knee.

FIG. 34 shows the vertical section (cv) passing through the centre of the final adjustment bar 130 following its longitudinal axis and explains the positioning of the sighting unit relative to the final adjustment bar 130. From now on, it is understood that the sighting unit 160 is put into place relative to the final adjustment bar 130 by making the first slit 165 correspond to the final adjustment bar 130 and aligning the opening created by the intersection of the slits 64, 65 with the localization dog point 134. The dimensions of the first slit 165 are calibrated with the diameter of the final adjustment bar 130 in order to allow the tight sliding of the guide 160 relative to the final adjustment bar 130, so that the symmetry plane (omega) of the second slit is strictly perpendicular to the final adjustment bar 130. Moreover, the diameter of the localization dog point 34 is calibrated in order to correspond to the opening created by the intersection of the slits 164, 165, so that there is no parasite translation of the sighting unit 160 along the main axis of the final adjustment bar 130 and thus, the symmetry plane (Omega) of the second slit 164 is exactly in the middle of the segment that separated the revolution axis (Bêta, Gamma) of the drilling supports 131, 132.

FIG. 35 shows the installation of an alignment bar 168 along the second slit 164. The diameter of the alignment bar 168 is calibrated with the second slit 164 and therefore the main axis of the alignment bar 168 belongs to the Omega plane of the second slit 164.

FIG. 36 explains the change of configuration of the instrument for the passage for the search of the femoral's head centre, from the frontal plane to the sagittal plane. There is a pitching screw 171, which allows the clutch of the angular transmission 170 with the end of the adjusting bar 120. The unscrewing of the pitching screw about its rotation axis (Téta) allows the swinging of the angular transmission 170 and of the final adjusting rod 130 relative to the adjusting rod 120 and consequently turn upside down the plane delimited by the revolution axes (Beta, Gamma) from perpendicular to the front plane of the patient (represented by the plane XY) to perpendicular to the patient's sagittal plan (represented by the plane XZ). Once obtained the transition from a plane to another one, it is enough to screw back the blocking screw 171.

FIG. 37 explains the available adjustments for adjusting the primary adjustment set 140 and the secondary adjustment set 150 according to a referential system connected to the surgery table 100:

Vise assembly 90 can translate all along the main axis of the table 100: Tx The rigid bar can translate perpendicularly relative to vise assembly 90: Tz The secondary adjustment set 150 can translate relative to rigid bar 110 all along the opening 113 of the support 111: T alpha.

The secondary adjustment set 150 can rotate about the rigid bar 110: Rz

The final adjustment bar 130 can rotate about the revolution axis (Beta) of the drilling guide 132 R beta.

After having handled the articulation of the elements, the stopping systems, shown here by the lock-up clamping levers 92, 91, 112, 133, prevent the falling apart of the bar system 110, 120, 130 and the vise assembly 90.

In the present case, the instrument is used for searching the femoral's head centre in the frontal plane, therefore the plane defined by the revolution axis (Beta, Gamma) is perpendicular to the frontal plane (represented by plan XY)

FIG. 38 shows that the available adjustments in the sagittal plane are identical to those available in the frontal plane, with the difference that the plane defined by the revolution axis (Beta, Gamma) is perpendicular to the sagittal plane of the patient (represented by plan XZ).

FIGS. 13, 20, 39-42 explain the technique of use of the instrument:

The patient is classically accommodated in dorsal decubitus positioning.

One will have to make sure that the fastening rail provided for the surgery table's accessories is protruding enough in order to allow palpation through sterile spaces subsequent to their arrangement.

Otherwise, a supplementary rail segment can be fixed on the original rail so that this piece can be easily palpated once the surgical field has been arranged, for the purpose of easily fastening the sterile jaw vise 90 carrying the instrument.

Subsequent to the setting into place of the sterile areas, the knee is handled using the usual technique.

The knee joint being exposed, the sterile clamp 90 is positioned, which is fixed to the rail 100 of the surgical table, above the surgical field (reinforcing them if necessary at the fastening point by a plastic self-adhesive part).

The position of the clamp 90, the rigid bar 10 and the adjustment bar 120 are adjusted so that the final adjustment bar 130 (considering the instrument configured for a search of the femoral head's centre in the frontal plane) extends above the patient's knee by about 15 cm cranially (towards the head) relative to the joints interline in the horizontal plane (FIG. 13) and by around 5 cm above the knee in the vertical plane (FIG. 14).

At the beginning, the clamping levers 92, 91, 112, 133 are unblocked and consequently vise assembly 90 can translate freely all along the rail 101 of the surgery table 100, the rigid bar 110 can vertically translate, the secondary adjustment set 150 can translate along the main axis (alpha) of the opening 113 of the guide 111, the secondary adjustment set 150 can rotate about the rigid bar 110 and finally, the final adjustment bar 130 can rotate about the revolution axis (Beta) of the first drilling guide 132. The surgeon uses these adjustments to obtain the desired position of the final adjustment bar 130 as previously explained, and locks the clamping levers 92, 91, 112 in order to block the adjustments.

Figure 39:
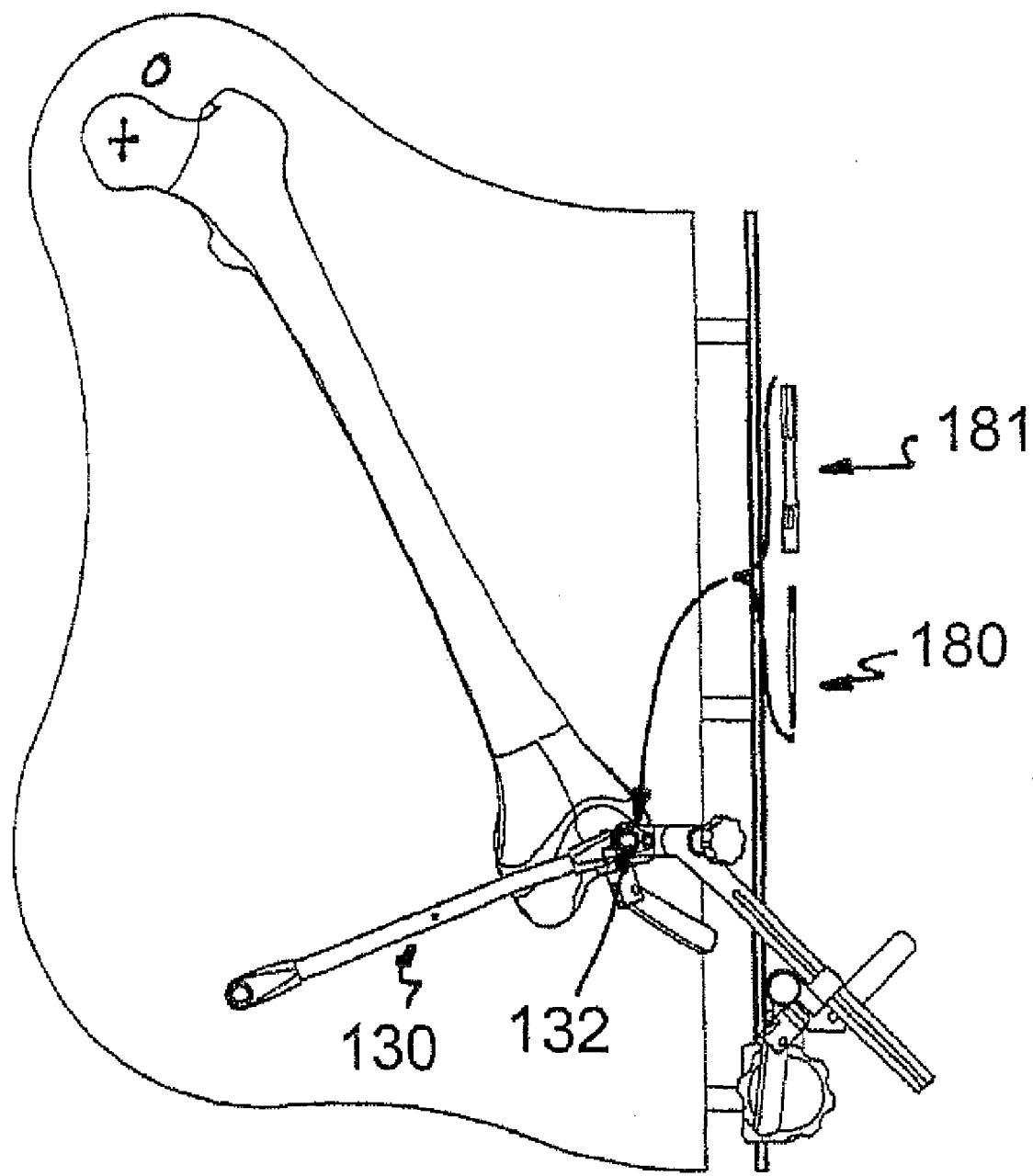
Figure 40:
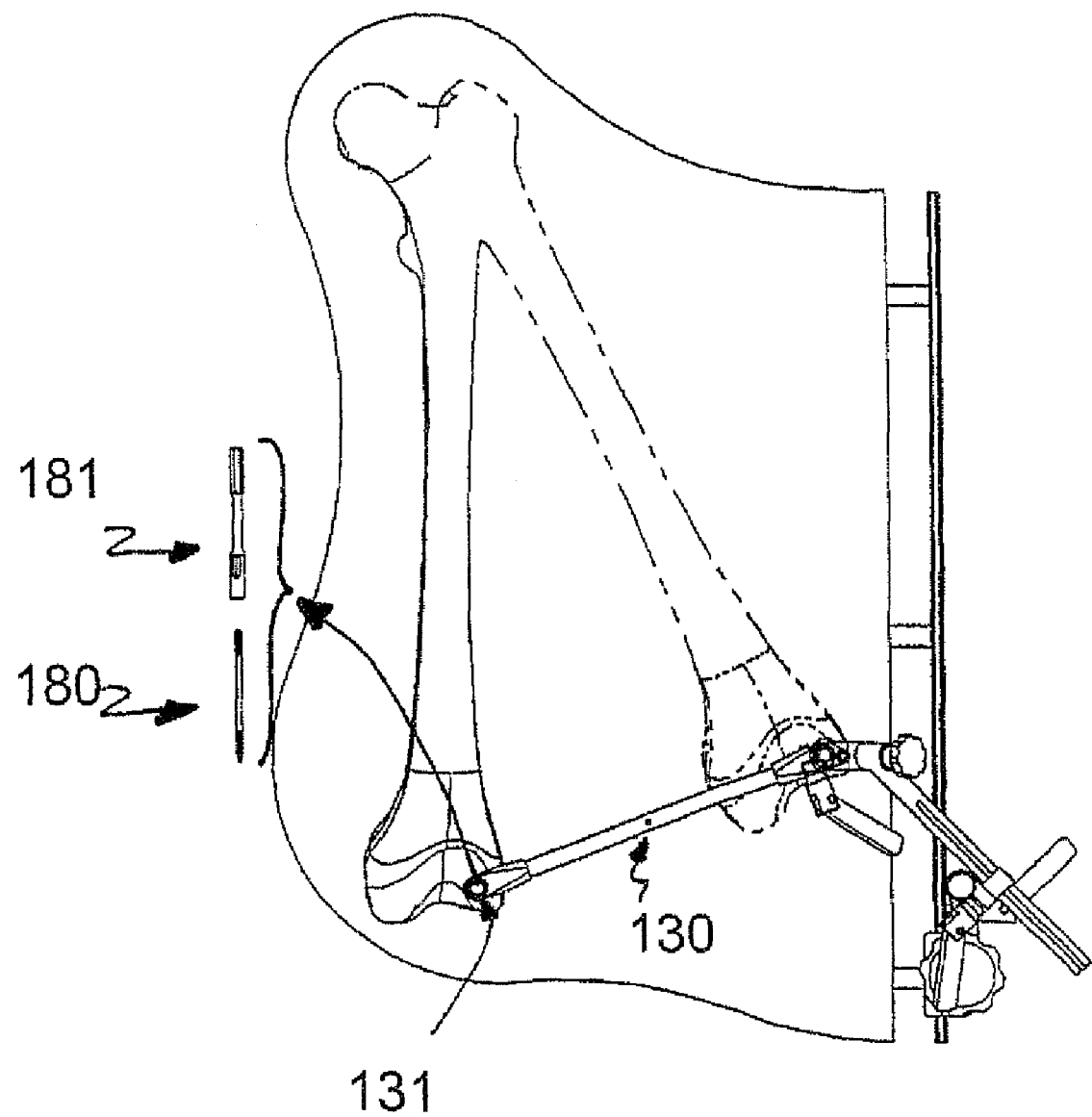

The knee is brought under the first drilling support 132 and the threaded spindle 80 is introduced in the patient's knee G along the revolution axis (Beta), with the help of the spindle 181 guided by its cylindrical section 180 along the internal orifice 135b and perpendicularly to the plane defined by the surgery table 100 (FIG. 39).

The selection of the insertion site for the spindle 180 is entirely free, but once the location has been selected, this location should be vitally "kept in memory".

The surgeon rotates the inferior limb of the patient in the frontal plane and brings the knee G under the second guide 131, the final adjustment bar 130 being always free to rotate about the axis (Bêta) of the first drilling guide 132 which allows an easy adjustment of its location in space (FIG. 39).

The adjustment is correct when the cylindrical section 182 of the spindle 81 "finds" the axis of the threaded spindle previously introduced in the knee G, which allows, at this moment, its extraction from knee G.

Before taking out the spindle 181, it is mandatory to lock-up the clamping lever 133 in order to preserve the "memory" of the location of the threaded spindle in position 2 of the knee (=F2). The location in space of the second point belonging to the arc of circle described by the spindle when the knee is fixed in position P2 (=F2) is thus determined. It is well-understood that the system of articulated bars is now completely rigid relative to the surgery table.

The sighting unit 160 is now put into place along the final adjustment bar 130 and centered with the localization dog point 134. The alignment rod 168 can be equally put into place in the second slit 164 of the sighting unit 160.

By construction, the symmetry plan (Omega) of the second slit 164 that includes the revolution axis of the cylindrical tenon 163 of the sighting unit 160 and that of the axis of the alignment bar 168 indicates the orientation of the perpendicular passing exactly through the centre of the segment of the revolution axis (Bêta, Gamma) of the drilling guides 131, 132, thus indicating in a very precise manner the direction of the femoral head's centre (O).

The knee middle point G is then brought to the vertical of the cylindrical tenon 163 or of the alignment bar 168 thus materializing the femoral mechanical axis (3×) (FIG. 41).

Two pins 182, 183 can then be fixed through the internal orifices 161, 162 of the sighting guide 160. By construction, the two pins 161, 162 define a perpendicular plane relative to the femoral mechanical axis (3×).

In FIG. 42, it is shown that the centre of the femoral head (O) belongs to the symmetry plane (Omega) of the second slit 64.

If needed, the surgeon can unlock the lever 171 of the articular transmission 170. The unscrewing of the blocking screw 71 about its rotation axis (Téta) allows the angular transmission 170 and the final adjustment bar 130 to rotate with respect to the adjustment bar 120 and consequently to swing the plane defined by the revolution axis (Bêta, Gamma), from perpendicular to the frontal plane of the patient to perpendicular to the sagittal plane of the patient, which allows the surgeon to determine the centre of the femoral head in the sagittal plane according to a method similar to the one explained for the determination of the centre of the femoral head in the frontal plane.

After determining the centre of the femoral head (O) in the frontal plane (and thus determining the mechanical axis (3×1)) and potentially determining the centre of the femoral head (O) in the sagittal plane, the surgeon can unlock the clamping lever 91 of the vise assembly 90 and take away vertically the bar set 110, 120, 130 as well as the sighting guide 160 and the alignment bar 168.

The instruments for femoral distal cutting which are oriented by the pins placed during the determination of the femoral head's centre (O) will thus allow the obtention of a distal cutting strictly perpendicular to the femoral mechanical axis.

FIG. 43 discloses another embodiment avoiding the need to attach a vise assembly 90 to the rail 101 of the surgical table 100. This different embodiment is outlined in the form of a fastening clamp 210 provided with lateral pinching elements 211, 212 to be attached to the pelvis or to the rib case of the patient. By the action of a known mechanism (not represented) such as a endless screw, the lateral pinching elements 211, 212 can be tightened (that is to say can move one towards the other) and be blocked against the patient. Thus the fastening clamp 210 is completely attached to the patient. Because the fastening clamp 210 has a large plate 214 in contact with the surgery table and the rigid bar 110 is perpendicular relative to this plate 114, the rigid bar 110 is therefore vertical. The articulated bar system 110, 120, 130 is similar to the previous embodiment. The bar adjustment system 110, 120, 130 is also similar to the previous embodiment, with the only difference that the guide 111 can also be moved vertically along the rigid bar 110.

It is also possible to devise a hybrid solution (not illustrated) made up of lateral clamps attached to each side of the table and locking-up the patient.

FIG. 44 illustrates, schematically, the principle according to another embodiment, resorting to an a pantograph-type assembly consisting of diamond-shaped four articulated arm construction, where two opposite angles 51, 52 define an axis in which the guiding rod 53 can freely slide. An alternative system for the pantograph-type assembly is illustrated in FIG. 26. One of the angles 58 of the diamond-shaped assembly is fixed in rotation to an arm 57 itself fixed, possibly in rotation, to an element 55 of the surgery table. A rod 53 connecting two opposite angles will always pass perpendicularly through the middle of the straight line segment (diagonal) connecting the two other angles (58, 59), immobilized after the localization in F1 and F2, of the quadrilateral.

The blocking of the axis at F1 is enough to fix the orientation of the rod 53.

According to yet another variant whose principle is illustrated in FIG. 45, a bar 60 may be provided, in the form of an arm, preferably a graduated bar, perpendicular or not to the axis 55 of the surgery table, this arm being fixed or rotatable at 64. This arm comprises a first localization means 61. The second localization means 62 is fixed on a telescopic bar 63 being able to retract at least partially and to be immobilized in the arm 60. A member 65, for example of the slider type, with the sighting device can slide on bar 63 and be brought at the centre of the two localization means 61, 62, themselves being immobilized after the detection of points F1 et F2 of the same point of the knee in position P1 and P2.

The invention claimed is:

1. An instrument for the determination of a plane containing the mechanical axis of the femur of an inferior limb comprising a device in which there is provided:
a mechanical means made of articulated and/or sliding elements in order to determine and memorize two positions, freely selected, in space (F1 and F2) of the same point (F) of the knee, when said knee is brought in positions P1 and P2, relative to a referential system, positions being obtained by rotation of the inferior limb from the position P1 towards the position P2, about the centre of the femoral head,
a means for materializing an orientation of a plane omega passing through the middle of a line segment defined by the two said positions F1 and F2, perpendicular to this segment and containing the centre of the femoral head.

2. The instrument according to claim 1 wherein there is provided for the memorization of points F1 and F2 at least one means of mechanical immobilization of an articulated bar supported by a device with at least three degrees of liberty and comprising at least two localization means of said freely selected point F of the knee.

3. The instrument according to claim 2 wherein the device comprises a degree of rotation about a perpendicular axis to the sagittal or frontal plane.

4. The instrument according to claim 3 wherein the localization means are hollow cylindrical elements able to be precisely positioned above a fixed mark located at point F of the knee.

5. The instrument according to claim 4 wherein the mark is provided by the action of a laser beam, a pen or a surgery marker, or an electrical lancet.

6. The Instrument according to claim 2 wherein the localization means comprise drilling or marking guides.

7. The instrument according to claim 6 wherein the mark is a pin, possibly threaded.

8. The instrument according to claim 2 wherein the means for materializing the orientation of the omega plane is a mechanical means allowing the orientation of a direction element at the middle and perpendicular to the straight line segment separating the two localization means.

9. The instrument according to claim 8 wherein there is furthermore provided a means allowing to carry and fix the direction element of the aforementioned centre of the femoral head on the femur.

10. The instrument according to claim 9 wherein the direction element is a rod.

11. The instrument according to claim 10 wherein the rod is fixed to the femur and can be disconnected from the remainder of the device.

12. Instrument according to claim 2 wherein one of the localization means is located on a sliding arm in or along another arm fixed to the said referential system and comprising the other localization means.

13. The instrument according to claim 1 wherein the referential system is a surgery table.

14. The instrument according to claim 1 wherein the referential system is the pelvis associated to said femur.

15. Instrument according to claim 1 wherein the mechanical means of articulated elements comprises four articulated rods forming a parallelogram whose two opposite angles are provided with localization means, one of the angles being attached to the said referential system, and the two other angles being associated to the means for determining the omega plane's orientation.

16. The instrument according to claim 1 characterized in that it is constituted of a first adjustment set of articulated elements and a second adjustment set of articulated elements, the second set being provided with a final adjustment bar with the localization means, the second set being able to rotate about an angle of 90φ so that the final adjustment bar can pass from a frontal plane to a sagittal plane.

17. An instrument for determining a plane containing the mechanical axis of the femur comprising:

a mechanical means of articulated bars comprising an arm whose two points can be freely immobilized each in a position fixed and constant respectively to two positions in the space (F1 et F2) of a freely selected same point (F) of the knee, when said knee is in two different positions (P1 et P2) in the frontal or sagittal plane, a means for materializing the orientation of a plane passing through the middle of the straight line segment defined by the two aforementioned positions F1 and F2, perpendicular to this segment and containing the centre of the femoral head.

18. A method for the determination of the mechanical axis of the inferior limb comprising the steps of:

determining and memorizing, by a mechanical means of articulated or sliding bars, two points in the space (F1, F2) of the same freely selected point (F) of the knee, in two positions P1 and P2, relative to a surgery table or to the pelvis of the patient, the said positions being obtained by rotation of the inferior limb in the frontal or sagittal plane, about the centre of the hip, orientating a rod in the middle and perpendicularly to the straight line separating the two localization means immobilized during the determination of points (F1, F2).

19. The method according to the claim 18, characterized in that the mechanical means of articulated bars is made up of a quadrilateral attached to the surgery table, wherein one of the sides is, after adjustment, rigidly fixed relative to said table, and the opposite side has a length equal to the distance, separating points F1 and F2 to be determined, the side ends and the two other sides being articulated about two hollow axis.

20. The method according to claim 19 wherein the determination of points F1 and F2 is done by the fixation in the knee, through a first axis, of a pin at a freely selected point F in the position P1 of the knee (=F1), an adjacent side being then rigidly fixed, for example by a clamping lever or by a wing nut, at the rigid side, the knee is then brought to a position P2 by strict immobilization in the frontal or sagittal plane, position that is matched, by manipulation of the quadrilateral, to the other hollow axis of the side, in such a way that the pin can be retracted through the aforementioned hollow axis, the second position thus determined being memorized by rigid fixation of the adjacent side, for example by locking the wing nuts at the rigid side, the quadrilateral being then totally rigid and the centre of each axis situated at the two side extremities determining positions F1 and F2.

21. The method according to claim 18 wherein the determination of points F1 and F2 is done by fixating at position P1 and by taking away at position P2 a pin to or from a freely selected point F of the knee, through an hollow axis provided in the localization means.

22. The method according to claim 18 wherein the rod is inserted perpendicularly and at the middle of the side in a support.

23. The method according to claim 22 comprising the step wherein the knee is mobilized in the frontal plane until its centre is located in the precise alignment of the rod's direction which is then fixed by holding elements, for example nails, on the femur, and is then disconnected from the support so that it keeps the orientation of the mechanical axis of the inferior limb after the removal of the mechanical means of articulated bars.

* * * * *